United States Patent
Swayze et al.

(10) Patent No.: US 9,428,750 B2
(45) Date of Patent: Aug. 30, 2016

(54) OLIGOMERIC COMPOUNDS COMPRISING TRICYCLIC NUCLEOSIDES AND METHODS FOR THEIR USE

(71) Applicant: Ionis Pharmaceuticals, Inc., Carlsbad, CA (US)

(72) Inventors: Eric E. Swayze, Encinitas, CA (US); Andrew M. Siwkowski, Carlsbad, CA (US); Punit P. Seth, Carlsbad, CA (US); Thazha P. Prakash, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/628,044

(22) Filed: Feb. 20, 2015

(65) Prior Publication Data

US 2015/0259681 A1 Sep. 17, 2015

Related U.S. Application Data

(63) Continuation of application No. 13/848,623, filed on Mar. 21, 2013, now Pat. No. 8,993,528, which is a continuation of application No. 12/922,832, filed as application No. PCT/US2009/037686 on Mar. 19, 2009, now Pat. No. 8,426,378.

(60) Provisional application No. 61/150,501, filed on Feb. 6, 2009, provisional application No. 61/038,675, filed on Mar. 21, 2008.

(51) Int. Cl.
| | |
|---|---|
| C12N 15/11 | (2006.01) |
| C12N 15/113 | (2010.01) |
| A61K 31/712 | (2006.01) |
| A61K 31/7125 | (2006.01) |
| C07H 21/04 | (2006.01) |
| C07H 19/10 | (2006.01) |
| A61K 31/7052 | (2006.01) |
| A61K 31/7088 | (2006.01) |
| A61K 31/7042 | (2006.01) |

(52) U.S. Cl.
CPC ........... *C12N 15/113* (2013.01); *A61K 31/712* (2013.01); *A61K 31/7125* (2013.01); *C07H 19/10* (2013.01); *C07H 21/04* (2013.01); *A61K 31/7042* (2013.01); *A61K 31/7052* (2013.01); *A61K 31/7088* (2013.01); *C12N 2310/11* (2013.01); *C12N 2310/314* (2013.01); *C12N 2310/316* (2013.01); *C12N 2310/3125* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. |
| 4,415,732 A | 11/1983 | Caruthers |
| 4,458,066 A | 7/1984 | Caruthers |
| 4,469,863 A | 9/1984 | Tso |
| 4,476,301 A | 10/1984 | Imbach |
| 4,500,707 A | 2/1985 | Caruthers |
| 4,668,777 A | 5/1987 | Caruthers et al. |
| 4,725,677 A | 2/1988 | Koster |
| 4,845,205 A | 7/1989 | Huynh Dinh et al. |
| 4,973,679 A | 11/1990 | Caruthers |
| 4,981,957 A | 1/1991 | Lebleu |
| 5,013,830 A | 5/1991 | Ohtsuka |
| 5,023,243 A | 6/1991 | Tullis |
| 5,034,506 A | 7/1991 | Summerton |
| 5,118,800 A | 6/1992 | Smith |
| 5,130,302 A | 7/1992 | Spielvogel |
| 5,132,418 A | 7/1992 | Caruthers |
| 5,134,066 A | 7/1992 | Rogers |
| RE34,069 E | 9/1992 | Koster et al. |
| 5,149,797 A | 9/1992 | Pederson |
| 5,166,315 A | 11/1992 | Summerton |
| 5,175,273 A | 12/1992 | Bischofberger |
| 5,177,196 A | 1/1993 | Meyer, Jr. |
| 5,177,198 A | 1/1993 | Spielvogel |
| 5,185,444 A | 2/1993 | Summerton |
| 5,188,897 A | 2/1993 | Suhadolnik |
| 5,194,599 A | 3/1993 | Froehler |
| 5,214,134 A | 5/1993 | Weis |
| 5,216,141 A | 6/1993 | Benner |
| 5,220,007 A | 6/1993 | Pederson |
| 5,235,033 A | 8/1993 | Summerton |
| 5,256,775 A | 10/1993 | Froehler |
| 5,264,423 A | 11/1993 | Cohen |

(Continued)

FOREIGN PATENT DOCUMENTS

| | | |
|---|---|---|
| WO | WO 94/02499 | 2/1994 |
| WO | WO 94/17093 | 8/1994 |

(Continued)

OTHER PUBLICATIONS

Steffens et al. J. Am. Chem. Soc. (1997), vol. 119, pp. 11548-11549.*

(Continued)

*Primary Examiner* — Patrick Lewis
(74) *Attorney, Agent, or Firm* — Ionis Pharmaceuticals, Inc. Patent Dept.

(57) ABSTRACT

The present disclosure provides tricyclic nucleosides, oligomeric compounds comprising at least one of the tricyclic nucleosides and methods of using the oligomeric compounds. The methods provided herein include contacting a cell or administering to an animal at least one of the oligomeric compounds. In certain embodiments, the oligomeric compounds hybridize to a portion of a target RNA resulting in loss of normal function of the target RNA.

18 Claims, No Drawings

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,319,080 A | 6/1994 | Leumann |
| 5,321,131 A | 6/1994 | Agrawal |
| 5,359,044 A | 10/1994 | Cook |
| 5,366,878 A | 11/1994 | Pederson |
| 5,367,066 A | 11/1994 | Urdea |
| 5,378,825 A | 1/1995 | Cook |
| 5,386,023 A | 1/1995 | Sanghvi |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton |
| 5,405,939 A | 4/1995 | Suhadolnik |
| 5,432,272 A | 7/1995 | Benner |
| 5,434,257 A | 7/1995 | Matteucci |
| 5,446,137 A | 8/1995 | Maag |
| 5,453,496 A | 9/1995 | Caruthers |
| 5,455,233 A | 10/1995 | Spielvogel |
| 5,457,187 A | 10/1995 | Gmeiner |
| 5,459,255 A | 10/1995 | Cook |
| 5,466,677 A | 11/1995 | Baxter |
| 5,466,786 A | 11/1995 | Buhr |
| 5,470,967 A | 11/1995 | Huie |
| 5,476,925 A | 12/1995 | Letsinger |
| 5,484,908 A | 1/1996 | Froehler |
| 5,489,677 A | 2/1996 | Sanghvi |
| 5,491,133 A | 2/1996 | Walder |
| 5,502,177 A | 3/1996 | Matteucci |
| 5,508,270 A | 4/1996 | Baxter |
| 5,514,785 A | 5/1996 | Van Ness |
| 5,519,126 A | 5/1996 | Hecht |
| 5,519,134 A | 5/1996 | Acevedo |
| 5,525,711 A | 6/1996 | Hawkins |
| 5,527,899 A | 6/1996 | Froehler |
| 5,536,821 A | 7/1996 | Agrawal |
| 5,541,306 A | 7/1996 | Agrawal |
| 5,541,307 A | 7/1996 | Cook |
| 5,550,111 A | 8/1996 | Suhadolnik |
| 5,552,540 A | 9/1996 | Haralambidis |
| 5,561,225 A | 10/1996 | Maddry |
| 5,563,253 A | 10/1996 | Agrawal |
| 5,565,350 A | 10/1996 | Kmiec |
| 5,565,555 A | 10/1996 | Froehler |
| 5,567,811 A | 10/1996 | Misiura |
| 5,571,799 A | 11/1996 | Tkachuk |
| 5,576,427 A | 11/1996 | Cook |
| 5,587,361 A | 12/1996 | Cook |
| 5,587,469 A | 12/1996 | Cook |
| 5,591,722 A | 1/1997 | Montgomery |
| 5,594,121 A | 1/1997 | Froehler |
| 5,596,086 A | 1/1997 | Matteucci |
| 5,596,091 A | 1/1997 | Switzer |
| 5,597,909 A | 1/1997 | Urdea |
| 5,602,240 A | 2/1997 | De Mesmaeker |
| 5,608,046 A | 3/1997 | Cook |
| 5,610,289 A | 3/1997 | Cook |
| 5,610,300 A | 3/1997 | Altmann |
| 5,614,617 A | 3/1997 | Cook |
| 5,618,704 A | 4/1997 | Sanghvi |
| 5,623,065 A | 4/1997 | Cook |
| 5,623,070 A | 4/1997 | Cook |
| 5,625,050 A | 4/1997 | Beaton |
| 5,627,053 A | 5/1997 | Usman |
| 5,633,360 A | 5/1997 | Bischofberger |
| 5,639,873 A | 6/1997 | Barascut |
| 5,645,985 A | 7/1997 | Froehler |
| 5,646,265 A | 7/1997 | McGee |
| 5,646,269 A | 7/1997 | Matteucci |
| 5,652,355 A | 7/1997 | Metelev |
| 5,652,356 A | 7/1997 | Agrawal |
| 5,663,312 A | 9/1997 | Chaturvedula |
| 5,670,633 A | 9/1997 | Cook |
| 5,672,697 A | 9/1997 | Buhr |
| 5,677,437 A | 10/1997 | Teng |
| 5,677,439 A | 10/1997 | Weis |
| 5,681,941 A | 10/1997 | Cook |
| 5,700,920 A | 12/1997 | Altmann |
| 5,700,922 A | 12/1997 | Cook |
| 5,721,218 A | 2/1998 | Froehler |
| 5,750,692 A | 5/1998 | Cook |
| 5,763,588 A | 6/1998 | Matteucci |
| 5,792,608 A | 8/1998 | Swaminathan |
| 5,792,847 A | 8/1998 | Buhr et al. |
| 5,830,653 A | 11/1998 | Froehler |
| 6,005,096 A | 12/1999 | Matteucci |
| 6,426,220 B1 | 7/2002 | Bennett et al. |
| 6,600,032 B1 | 7/2003 | Manoharan et al. |
| 7,399,845 B2 | 7/2008 | Seth et al. |
| 7,427,672 B2 | 9/2008 | Imanishi et al. |
| 2004/0171570 A1 | 9/2004 | Allerson et al. |
| 2005/0130923 A1 | 6/2005 | Bhat et al. |

FOREIGN PATENT DOCUMENTS

| | | |
|---|---|---|
| WO | WO 99/14226 | 3/1999 |
| WO | WO 02/36743 | 5/2002 |
| WO | WO 2005/028628 | 3/2005 |
| WO | WO 2005/121371 | 12/2005 |
| WO | WO 2005/121372 | 12/2005 |
| WO | WO 2007/131238 | 11/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Ittig et al. Nucleic Acids Research (2004), vol. 32, pp. 346-353.*
Bielinska et al. Science (1990), vol. 250, pp. 997-1000.*
Kalota et al. Nucleic Acids Research (2006), vol. 34, pp. 451-461.*
Aboul-Fadl, "Antisense Oligonucleotides: The State of the Art" Current Medicinal Chemistry, Bentham Science Publishers (2005) 12(19):2193-2214.
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Brazma et al., "Gene expression data analysis" FEBS Lett. (2000) 480:17-24.
Carulli et al., "High Throughput Analysis of Differential Gene Expression" J. Cell. Biochem. Suppl. (1998) 31:286-296.
Celis et al., "Gene expression profiling: monitoring transcription and translation products using DNA microarrays and proteomics" FEBS Lett (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
Elbashir et al., "Duplexes of 21-nucleotide RNAs mediate RNA interference in cultured mammalian cells" Nature (2001) 411:494-498.
Elbashir et al., "RNA interference is mediated by 21- and 22-nucleotide RNAs" Genes Dev. (2001) 15:188-200.
Englisch et al., "Chemically Modified Oligonucleotides as Probes and Inhibitors" Angewandte Chemie, International Edition (1991) 30:613.

(56) References Cited

OTHER PUBLICATIONS

Fire et al., "Potent and Specific Genetic Interference by Double-Stranded RNA in Caenorhabditis Elegans" Nature (1998) 391:806-811.
Fuchs et al., "Identification of Differentially Expressed Genes by Mutually Subtracted RNA Fingerprinting" Anal. Biochem. (2000) 286:91-98.
Gait et al., Applications of Chemically Synthesized RNA in RNA: Protein Interactions, Ed. Smith (1998) 1-36.
Gallo et al., "2'-C-Methyluridine phosphoramidite: a new building block for the preparation of RNA analogues carrying the 2'-hydroxyl group" Tetrahedron (2001) 57:5707-5713.
Going et al., "Molecular Pathology and Future Developments" Eur. J. Cancer. (1999) 35:1895-1904.
Guzaev et al., "A Conformationally Preorganized Universal Solid Support for Efficient Oligonucleotide Synthesis" J. Am. Chem. Soc. (2003) 125:2380-2381.
Ittig et al., "Nuclear antisense effects in cyclophilin A pre-mRNA splicing by oligonucleotides: a comparison of tricyclo-DNA with LNA" Nucleic Acids Research (2004) 32(1):346-353.
Ittig et al., "Oligonucleotide Analogues: From Supramolecular Principles to Biological Properties" Collection Symposium Series (2005) 7:21-26.
Ivanova et al., "Tricyclo-DNA Containing Oligonucleotides as Steric Block Inhibitors of Human Immunodeficiency Virus Type 1 Tat-Dependent Trans-Activation and HIV-1 Infectivity" Oligonucleotides (2007) 17(1):54-65.
Jones et al., "RNA Quantitation by Fluorescence-Based Solution Assay: RiboGreen Reagent Characterization" Analytical Biochemistry (1998) 265:368-374.
Jungblut et al., "Proteomics in human disease: Cancer, heart and infectious diseases" Electrophoresis (1999) 20:2100-2110.
Jurecic et al., "Long-distance DD-PCR and cDNA microarrays" Curr. Opin. Microbiol. (2000) 3:316-321.
Kroschwitz, The Concise Encyclopedia of Polymer Science and Engineering (1990), pp. 858-859, John Wiley & Sons.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotechnol. (2000) 80:143-157.
Leumann, "DNA analogues: From supramolecular principles to biological properties" Bioorganic and Medicinal Chemistry (2002) 10(4):841-854.
Madden et al., "Serial analysis of gene expression: from gene discovery to target identification" Drug Discov. Today (2000) 5:415-425.
Miura et al., "Fluorometric determination of total mRNA with oligo(dT) immobilized on microtiter plates" Clin. Chem. (1996) 42(11):1758-1764.
Montgomery et al., "RNA as a target of double-stranded RNA-mediated genetic interference in Caenorhabditis elegans" PNAS (1998) 95:15502-15507.
Nishikura et al., "A Short Primer on RNAi: RNA-Directed RNA Polymerase Acts as a Key Catalyst" Cell (2001) 107:415-416.
Prashar, "READS: A Method for Display of 3'-End Fragments of Restriction Enzyme-Digested cDNAs for Analysis of Differential Gene Expression" Methods Enzymol. (1999) 303:258-272.
Renneberg et al., "Watson-Crick Base-Pairing Properties of Tricyclo-DNA" J. Am. Chem. Soc. (2002) 124:5993-6002.
Sanghvi, Antisense Research & Applications, Chapter 15, Crooke and Lebleu ed. CRC Press, 1993.
Scaringe, "RNA Oligonucleotide Synthesis via 5'-Silyl-2'-Orthoester Chemistry" Methods (2001) 23:206-217.
Scheidegger et al., "Synthesis and Pairing Properties of Alpha-Tricyclo-DNA" Chemistry (2006) 12:8014-8023.
Steffens et al., "Nucleic-Acid Analogs with Constraint Conformational Flexibility in the Sugar-Phosphate Backbone 'Tricyclo-DNA'" Helvetica Chimica Acta (1997) 80:2426-2439.
Steffens et al., "Tricyclo-DNA: A Phosphodiester-Backbone Based DNA Analog Exhibiting Strong Complementary Base-Pairing Properties" J. Am. Chem. Soc. (1997) 119:11548-11549.
Steffens et al., "Synthesis and Thermodynamic and Biophysical Properties of Tricyclo-DNA" J. Org. Chem. (1999) 121(14):3249-3255.
Sutcliffe et al., "TOGA: An automated parsing technology for analyzing expession of nearly all genes" PNAS (2000) 97:1976-1981.
Tabara et al., "RNAi in C. elegans: Soaking in the Genome Sequence" Science (1998) 282:430-431.
Tijsterman et al., "RNA Helicase MUT-14-Dependent Gene Silencing Triggered in C. elegans by Short Antisense RNAs" Science (2002) 295:694-697.
Timmons et al., "Specific interference by ingested dsRNA" Nature (1998) 395:854.
Timmons et al., "Ingestion of bacterially expressed dsRNAs can produce specific potent genetic interference in Caenorhabditis elegans" Gene (2001) 263:103-112.
To, "Identification of Differential Gene Expression by High Throughput Analysis" Comb. Chem. High Throughput. Screen (2000) 3:235-241.
Tuschl et al., "Targeted mRNA degradation by double-stranded RNA in vitro" Genes Dev. (1999) 13:3191-3197.
Zamecnik et al., "Inhibition of Rous sarcoma virus replication and cell transformation by a specific oligodeoxynucleotide" PNAS (1978) 75:280-284.
Zhou et al., "Fine Tuning of Electrostatics around the Internucleotide Phosphate through Incorporation of Modified 2'.4'-Carbocyclic-LNAs and -ENAs Leads to Significant Modulation of Antisense Properties" J. Org. Chem. (2009) 74:118-134.
International Search Report for application PCT/US2009/037686 dated Jul. 22, 2009.
Geary et al. "Pharmacokinetics of phosphorothioate antisense oligodeoxynucleotides" Current Opinion in Investigational Drugs (2001) 2(4):52-573.
Ittig et al., "Position-dependent effects on stability in tricyclo-DNA modified oligonucleotide duplexes" Nucleic Acids Research (2011) 39(1):373-380.
Leumann, "Sugar modification as a means to increase the biological performance of oligonucleotides" Nucleic Acids Symposium Series (2006) 50:55-56.
European Search Report for application EP 09722456 dated Nov. 27, 2013.
Kang et al., "Inhibition of mdr1 gene expression by chimeric HNA antisense oligonucleotides" Nucleic Acids Research (2004) 32(14): 4411-4419.
Levin, "A review of issues in the pharmacokinetics and toxicology of phosphorothioate antisense oligonucleotides" Biochimica et biophysica acta. (1999) 1489(1): 69-84.
Murray et al., "TricycloDNA-modified oligo-2'-deoxyribonucleotides dreduce scavenger receptor B1 mRNA in hepatic and extra-hepatic tissues—a comparative study of oligonucleotide length, design and chemistry" Nucleic Acids Research (2012) 40(13): 6135-6143.
Seth et al., "Short Antisense Oligonucleotides with Novel 2'4'—Conformationally Restricted Nucleoside Analogues Show Improved Potency without Increased Toxicity in Animals" Journal of Medicinal Chemistry (2009) 52(1): 10-13.
Swayze et al., "Antisense oligonucleotides containing locked nucleic acid improve potency but cause significant hepatotoxicity in animals" Nucleic Acids Research (2007) 35(2): 687-700.

\* cited by examiner

OLIGOMERIC COMPOUNDS COMPRISING TRICYCLIC NUCLEOSIDES AND METHODS FOR THEIR USE

SEQUENCE LISTING

The present application is being filed along with a Sequence Listing in electronic format. The Sequence Listing is provided as a file entitled CHEM0049USC2SEQ_ST25.txt, created on Feb. 20, 2015, which is 8 Kb in size. The information in the electronic format of the sequence listing is incorporated herein by reference in its entirety.

FIELD OF THE INVENTION

The present disclosure provides tricyclic nucleosides, oligomeric compounds comprising the tricyclic nucleosides and methods of using the oligomeric compounds. The present methods include contacting a cell with, or administering to an animal, at least one of the oligomeric compounds provided herein. In certain embodiments, the oligomeric compounds hybridize to a portion of a target RNA resulting in loss of normal function of the target RNA.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with an antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, affinity, specificity or pharmacokinetics for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of tricyclic modified nucleosides has been reported in the literature (Steffens et al., Helvetica Chimica Acta, 1997, 80, 2426-2439). The synthesis of tricyclic modified nucleosides and their incorporation into oligomeric compounds has also been reported in the literature (Steffens et al., J. Am. Chem. Soc., 1997, 119, 11548-11549; Steffens et al., J. Org. Chem., 1999, 121 (14), 3249-3255; Renneberg et al., J. Am. Chem. Soc., 2002, 124, 5993-6002; Ittig et al., Nucleic Acids Research, 2004, 32 (1), 346-353; Scheidegger et al., Chemistry, 2006, 12, 8014-8023; and Ivanova et al., Oligonucleotides, 2007, 17, 54-65).

A single 5-8-5 (tc-DNA-DNA-tcDNA) Gapped oligomeric compound was prepared and annealed with $^{32}$P-radiolabeled complementary RNA. The resulting duplex was incubated with RNaseH with subsequent cleavage or the RNA (see Ittig et al., Collection Symposium Series, 2005, 7, 21-26). The 5-8-5 tc-DNA Gapped oligomeric compound was incubated with human and fetal calf serum and shown to have better stability than the equivalent duplex having unmodified DNA.

There remains a long-felt need for agents that specifically regulate gene expression via antisense mechanisms. Disclosed herein are antisense compounds and methods of their use for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify and exploit antisense compounds for these uses.

BRIEF SUMMARY OF THE INVENTION

Provided herein are tricyclic nucleosides, oligomeric compounds comprising at least one of the tricyclic nucleosides and methods of using the oligomeric compounds. The present methods include contacting a cell or administering to an animal at least one of the oligomeric compounds provided herein. In certain embodiments, the oligomeric compounds hybridize to a portion of a target RNA resulting in loss of normal function of the target RNA.

The variables are defined individually in further detail herein. It is to be understood that the tricyclic nucleoside incorporated into the oligomeric compounds provided herein include all combinations of the embodiments disclosed and variables defined herein.

In certain embodiments, methods are provided comprising contacting a cell with an oligomeric compound, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula II:

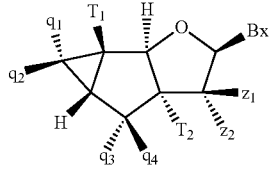

wherein independently for each of said tricyclic nucleosides having formula II:

Bx is a heterocyclic base moiety;

one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, O—$N(E_1)(E_2)$, $C(=O)N(E_1)(E_2)$, $C(=O)$—N$(E_3)$-$(CH_2)_r$—$N(E_1)(E_2)$ and $CH_2$—$N(H)$—$C(=NE_3)[N(E_1)(E_2)]$ wherein each $E_1$, $E_2$ and $E_3$ is, independently, H, $C_1$-$C_6$ alkyl or a protecting group and r is from 2 to about 6; and wherein said oligomeric compound comprises from about 8 to about 40 linked monomeric subunits and is complementary to at least a portion of a target RNA.

In certain embodiments, $q_3$ and $q_4$ are H for each of said tricyclic nucleosides having formula II. In certain embodiments, at least one of $q_1$, $q_2$, $q_3$ and $q_4$ is other than H for each of said tricyclic nucleosides having formula II. In certain embodiments, at least one of $q_1$, $q_2$, $q_3$ and $q_4$ is fluoro for each of said tricyclic nucleosides having formula II. In certain embodiments, at least one of $q_1$ and $q_2$ is fluoro for each of said tricyclic nucleosides having formula II. In certain embodiments, at least one of $q_3$ and $q_4$ is fluoro for each of said tricyclic nucleosides having formula II. In certain embodiments, $q_1$ and $q_2$ are each fluoro for each of said tricyclic nucleosides having formula II. In certain embodiments, at least one of $q_1$, $q_2$, $q_3$ and $q_4$ is $C_1$-$C_6$ alkyl for each of said tricyclic nucleosides having formula II. In certain embodiments, at least one of $q_1$, $q_2$, $q_3$ and $q_4$ is methyl for each of said tricyclic nucleosides having formula II. In certain embodiments, each $q_1$, $q_2$, $q_3$ and $q_4$ is H.

In certain embodiments, at least one of $z_1$ and $z_2$ is other than H for each of said tricyclic nucleosides having formula II. In certain embodiments, $z_1$ is fluoro for each of said tricyclic nucleosides having formula II. In certain embodiments, $z_2$ is fluoro for each of said tricyclic nucleosides having formula II. In certain embodiments, $z_1$ and $z_2$ are each fluoro for each of said tricyclic nucleoside having formula II. In certain embodiments, at least one of $z_1$ and $z_2$ is O—$C_1$-$C_6$ alkyl or substituted O—$C_1$-$C_6$ alkyl for each of said tricyclic nucleosides having formula II. In certain embodiments, $z_2$ is O—$C_1$-$C_6$ alkyl or substituted O—$C_1$-$C_6$ alkyl for each of said tricyclic nucleosides having formula II. In certain embodiments, each $z_1$ and $z_2$ is H.

In certain embodiments, each Bx is, independently, uracil, 5-methyluracil, thymine, cytosine, 5-methylcytosine, 2,6-diaminopurine, adenine or guanine.

In certain embodiments, the present methods include oligomeric compounds further comprising a 5' or 3'-terminal group. In certain embodiments, the present methods include oligomeric compounds further comprising a 5' and a 3'-terminal group.

In certain embodiments, wherein each linked monomeric subunit that is not a β-D-2'-deoxyribonucleoside or a tricyclic nucleoside having formula II is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, the oligomeric compounds used in the methods provided herein comprise a blockmer, a 3'-hemimer or 5'-hemimer. In certain embodiments, the oligomeric compounds used in the methods provided herein comprise a blockmer, a 3'-hemimer or 5'-hemimer wherein each monomeric subunit is, independently, a β-D-2'-deoxyribonucleoside or a tricyclic nucleosides having formula II.

In certain embodiments, the oligomeric compounds used in the methods provided herein comprise a gapped oligomeric compound comprising two external regions separated by an internal region wherein each external region independently comprises from 1 to 5 contiguous tricyclic nucleosides of formula II and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, each monomeric subunit in the internal region is a β-D-2'-deoxyribonucleoside.

In certain embodiments, the oligomeric compounds used in the methods provided herein comprise a gapped oligomeric compound comprising from about 8 to about 12 β-D-2'-deoxyribonucleosides. In certain embodiments, each external region comprises from 1 to 3 tricyclic nucleosides of formula II. In certain embodiments, the internal region comprises from about 10 to about 12 β-D-2'-deoxyribonucleosides. In certain embodiments, the internal region comprises from 11 to about 18 β-D-2'-deoxyribonucleosides. In certain embodiments, each external region comprises from 1 to 3 tricyclic nucleosides of formula II. In certain embodiments, the internal region comprises from 12 to about 14 β-D-2'-deoxyribonucleosides. In certain embodiments, each external region independently comprises from 1 to 3 tricyclic nucleosides of formula II. In certain embodiments, each external region comprises 2 tricyclic nucleosides of formula II. In certain embodiments, the internal region comprises 10 β-D-2'-deoxyribonucleosides.

In certain embodiments, the oligomeric compounds used in the methods provided herein comprise a tricyclic nucleoside of formula II at 5'-end and wherein the $T_1$ group of the 5'-terminal tricyclic nucleoside is a phosphate group.

In certain embodiments, each internucleoside linkage of the oligomeric compounds used in the methods provided herein is a phosphodiester. In certain embodiments, each internucleoside linkage of the oligomeric compounds used in the methods provided herein is a phosphorothioate. In certain embodiments, each internucleoside linkage of the oligomeric compounds used in the methods provided herein is, independently, a phosphodiester or a phosphorothioate. In certain embodiments, each internucleoside linkage of the oligomeric compounds used in the methods provided herein is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, the oligomeric compounds used in the methods provided herein comprise from 8 to about 18 linked monomeric subunits. In certain embodiments, the oligomeric compounds used in the methods provided herein comprise from 10 to about 16 linked monomeric subunits. In certain embodiments, the oligomeric compounds used in the methods provided herein comprise from 10 to about 14 linked monomeric subunits. In certain embodiments, the oligomeric compounds used in the methods provided herein comprise from 17 to about 26 linked monomeric subunits. In certain embodiments, the oligomeric compounds used in the methods provided herein comprise from 18 to about 21 linked monomeric subunits. In certain embodiments, the oligomeric compounds used in the methods provided herein comprise from 19 to about 20 linked monomeric subunits.

In certain embodiments, methods are provided comprising contacting a cell with an oligomeric compound, wherein the cell is in an animal. In certain embodiments, the cell is in a human.

In certain embodiments, methods are provided comprising contacting a cell with an oligomeric complementary to at least a portion of a target RNA wherein the target RNA is selected from mRNA, pre-mRNA and micro RNA. In certain embodiments, methods are provided comprising contacting a cell with an oligomeric complementary to at least a portion of a target RNA wherein the target RNA is mRNA. In certain embodiments, methods are provided comprising contacting a cell with an oligomeric complementary to at least a portion of a target RNA wherein the target RNA is human mRNA.

In certain embodiments, methods are provided comprising contacting a cell with an oligomeric complementary to at least a portion of a target RNA wherein the target RNA cleaved thereby inhibiting its function.

In certain embodiments, methods are provided comprising contacting a cell with an oligomeric complementary to at least a portion of a target RNA wherein the methods include evaluating the antisense activity of the oligomeric compound on said cell. In certain embodiments, the evaluating step comprises detecting the levels of target RNA. In certain embodiments, the evaluating step comprises detecting the levels of a protein. In certain embodiments, the evaluating comprises detection of one or more phenotypic effects.

In certain embodiments, the present methods comprise administering an oligomeric compound to an animal, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula II:

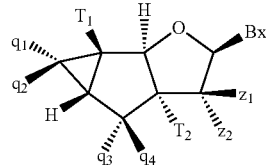

wherein independently for each of said tricyclic nucleosides having formula II:

Bx is a heterocyclic base moiety;
one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;
$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;
wherein each substituted group is, independently, mono or poly substituted with optionally protected substituent groups independently selected from halogen, oxo, $N_3$, CN, $OE_1$, $N(E_1)(E_2)$, O—$N(E_1)(E_2)$, C(=O)$N(E_1)(E_2)$, C(=O)—N$(E_3)$-$(CH_2)_r$—$N(E_1)(E_2)$ and $CH_2$—N(H)—C(=$NE_3$)[N$(E_1)(E_2)$] wherein each $E_1$, $E_2$ and $E_3$ is, independently, H, $C_1$-$C_6$ alkyl or a protecting group and r is from 2 to about 6; and
wherein said oligomeric compound comprises from about 8 to about 40 linked monomeric subunits and is complementary to at least a portion of a target RNA.

In certain embodiments, methods are provided comprising administering an oligomeric compound to a mammal. In certain embodiments, methods are provided comprising administering an oligomeric compound to a human.

In certain embodiments, methods are provided comprising administering an oligomeric compound to an animal wherein the oligomeric compound is complementary to at least a portion of a target RNA and the target RNA is selected from mRNA, pre-mRNA and micro RNA. In certain embodiments, the target RNA is mRNA. In certain embodiments, the target RNA is human mRNA.

In certain embodiments, methods are provided comprising administering an oligomeric compound to an animal wherein the oligomeric compound is complementary to at least a portion of a target RNA wherein the target RNA cleaved thereby inhibiting its function.

In certain embodiments, methods are provided comprising administering an oligomeric compound to an animal wherein the oligomeric compound is complementary to at least a portion of a target RNA wherein the methods include evaluating the antisense activity of the oligomeric compound on said cell. In certain embodiments, the evaluating step comprises detecting the levels of target RNA. In certain embodiments, the evaluating step comprises detecting the levels of a protein. In certain embodiments, the evaluating step comprises detection of one or more phenotypic effects.

In certain embodiments, oligomeric compounds are provided comprising at least one tricyclic nucleoside having formula II:

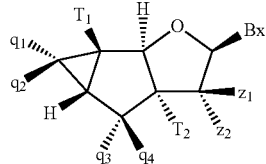

wherein independently for each of said tricyclic nucleosides having formula II:

Bx is a heterocyclic base moiety;

one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, O—$N(E_1)(E_2)$, $C(=O)N(E_1)(E_2)$, $C(=O)$—N$(E_3)$-$(CH_2)_r$—$N(E_1)(E_2)$ and $CH_2$—N(H)—$C(=NE_3)$[N$(E_1)(E_2)$] wherein each $E_1$, $E_2$ and $E_3$ is, independently, H, $C_1$-$C_6$ alkyl or a protecting group and r is from 2 to about 6; and wherein said oligomeric compound comprises from about 8 to about 40 linked monomeric subunits and is complementary to at least a portion of a target RNA.

In certain embodiments, oligomeric compounds are provided wherein $q_3$ and $q_4$ are H for each of said tricyclic nucleosides having formula II. In certain embodiments, at least one of $q_1$, $q_2$, $q_3$ and $q_4$ is other than H for each of said tricyclic nucleosides having formula II. In certain embodiments, at least one of $q_1$, $q_2$, $q_3$ and $q_4$ is fluoro for each of said tricyclic nucleosides having formula II. In certain embodiments, at least one of $q_1$ and $q_2$ is fluoro for each of said tricyclic nucleosides having formula II. In certain embodiments, at least one of $q_3$ and $q_4$ is fluoro for each of said tricyclic nucleosides having formula II. In certain embodiments, $q_1$ and $q_2$ are each fluoro for each of said tricyclic nucleosides having formula II. In certain embodiments, at least one of $q_1$, $q_2$, $q_3$ and $q_4$ is $C_1$-$C_6$ alkyl for each of said tricyclic nucleosides having formula II. In certain embodiments, at least one of $q_1$, $q_2$, $q_3$ and $q_4$ is methyl for each of said tricyclic nucleosides having formula II. In certain embodiments, each $q_1$, $q_2$, $q_3$ and $q_4$ is H.

In certain embodiments, oligomeric compounds are provided wherein at least one of $z_1$ and $z_2$ is other than H for each of said tricyclic nucleosides having formula II. In certain embodiments, $z_1$ is fluoro for each of said tricyclic nucleosides having formula II. In certain embodiments, $z_2$ is fluoro for each of said tricyclic nucleosides having formula II. In certain embodiments, $z_1$ and $z_2$ are each fluoro for each of said tricyclic nucleosides having formula II. In certain embodiments, at least one of $z_1$ and $z_2$ is O—$C_1$-$C_6$ alkyl or substituted O—$C_1$-$C_6$ alkyl for each of said tricyclic nucleosides having formula II. In certain embodiments, $z_2$ is O—$C_1$-$C_6$ alkyl or substituted O—$C_1$-$C_6$ alkyl for each of said tricyclic nucleosides having formula II. In certain embodiments, each $z_1$ and $z_2$ is H.

In certain embodiments, oligomeric compounds are provided wherein each Bx is, independently, uracil, 5-methyluracil, thymine, cytosine, 5-methylcytosine, 2,6-diaminopurine, adenine or guanine.

In certain embodiments, oligomeric compounds are provided comprising a 5' or 3'-terminal group. In certain embodiments, oligomeric compounds are provided comprising a 5' and a 3'-terminal group.

In certain embodiments, oligomeric compounds are provided wherein each linked monomeric subunit that is not a β-D-2'-deoxyribonucleoside or a tricyclic nucleoside having formula II is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, oligomeric compounds are provided wherein said oligomeric compound comprises a blockmer, a 3'-hemimer or 5'-hemimer. In certain embodiments, oligomeric compounds are provided comprising a blockmer, a 3'-hemimer or 5'-hemimer wherein each monomeric subunit is, independently, a β-D-2'-deoxyribonucleoside or a tricyclic nucleosides having formula II.

In certain embodiments, gapped oligomeric compounds are provided comprising two external regions separated by an internal region wherein each external region independently comprises from 1 to 5 contiguous tricyclic nucleosides of formula II and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, each monomeric subunit in the internal region is a β-D-2'-deoxyribonucleoside. In certain embodiments, the internal region comprises from about 8 to about 12 β-D-2'-deoxyribonucleosides. In certain embodiments, each external region comprises from 1 to 3 tricyclic nucleosides of formula II. In certain embodiments, the internal region comprises from about 10 to about 12 β-D-2'-deoxyribonucleosides. In certain embodiments, the internal region comprises from 11 to about 18 β-D-2'-deoxyribonucleosides. In certain embodiments, each external region comprises from 1 to 3 tricyclic nucleosides of formula II. In certain embodiments, the internal region comprises from 12 to about 14 β-D-2'-deoxyribonucleosides. In certain embodiments, each external region independently comprises from 1 to 3 tricyclic nucleosides of formula II. In certain embodiments, each external region comprises 2 tricyclic nucleosides of formula II. In certain embodiments, the internal region comprises 10 β-D-2'-deoxyribonucleosides. In certain embodiments, the oligomeric compound comprises a tricyclic nucleoside of formula II at 5'-end and wherein the $T_1$ group of the 5'-terminal tricyclic nucleoside is a phosphate group.

In certain embodiments, oligomeric compounds are provided wherein each internucleoside linkage is a phosphodiester. In certain embodiments, each internucleoside linkage is a phosphorothioate. In certain embodiments, each internucleoside linking group is, independently, a phosphodiester or a phosphorothioate. In certain embodiments, each internucleoside linking group is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, oligomeric compounds are provided comprising from 8 to about 18 linked monomeric subunits. In certain embodiments, oligomeric compounds are provided comprising from 10 to about 16 linked monomeric subunits. In certain embodiments, oligomeric compounds are provided comprising from 10 to about 14 linked monomeric subunits. In certain embodiments, oligomeric compounds are provided comprising from 17 to about 26 linked monomeric subunits. In certain embodiments, oligomeric compounds are provided comprising from 18 to about 21 linked monomeric subunits. In certain embodiments, oligomeric compounds are provided comprising from 19 to about 20 linked monomeric subunits.

In certain embodiments tricyclic nucleosides are provided having formula III:

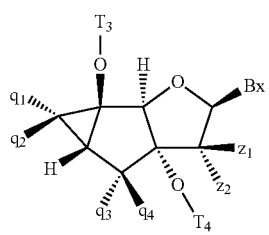

III wherein:

Bx is a heterocyclic base moiety;

one of $T_3$ and $T_4$ is H or a hydroxyl protecting group and the other of $T_3$ and $T_4$ is H, a hydroxyl protecting group or a reactive phosphorus group;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, O—$N(E_1)(E_2)$, C(=O)$N(E_1)(E_2)$, C(=O)—N$(E_3)$-$(CH_2)_r$—$N(E_1)(E_2)$ and $CH_2$—N(H)—C(=$NE_3$)[N$(E_1)(E_2)$] wherein each $E_1$, $E_2$ and $E_3$ is, independently, H, $C_1$-$C_6$ alkyl or a protecting group and r is from 2 to about 6; and wherein at least one of $q_1$, $q_2$, $q_3$, $q_4$, $z_1$ and $z_2$ is other than H.

In certain embodiments, Bx is uracil, 5-methyluracil, 5-thiazolo-uracil, 2-thio-uracil, 5-propynyluracil, thymine, 2'-thio-thymine, cytosine, 5-methylcytosine, 5-thiazolo-cytosine, 5-propynylcytosine, adenine, guanine, 2,6-diaminopurine, 1H-pyrimido[5,4-b][1,4]benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, 5-methyluracil, thymine, cytosine, 5-methylcytosine, adenine or guanine.

In certain embodiments, $T_3$ is acetyl, t-butyl, t-butoxymethyl, methoxymethyl, bicyclicyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl. In certain embodiments, $T_3$ is acetyl, benzyl, t-butyldimethylsilyl, t-butyldiphenylsilyl or dimethoxytrityl. In certain embodiments, $T_3$ is 4,4'-dimethoxytrityl.

In certain embodiments, $T_4$ is diisopropylcyanoethoxy phosphoramidite or H-phosphonate. In certain embodiments, $T_4$ is diisopropylcyanoethoxy phosphoramidite.

In certain embodiments, $T_3$ is 4,4'-dimethoxytrityl and $T_4$ is diisopropylcyanoethoxy phosphoramidite.

In certain embodiments, $q_3$ and $q_4$ are each H. In certain embodiments, at least one of $q_1$, $q_2$, $q_3$ and $q_4$ is other than H. In certain embodiments, at least one of $q_1$, $q_2$, $q_3$ and $q_4$ is fluoro. In certain embodiments, at least one of $q_1$ and $q_2$ is fluoro. In certain embodiments, at least one of $q_3$ and $q_4$ is fluoro. In certain embodiments, $q_1$ and $q_2$ are each fluoro. In certain embodiments, at least one of $q_1$, $q_2$, $q_3$ and $q_4$ is $C_1$-$C_6$ alkyl. In certain embodiments, at least one of $q_1$, $q_2$, $q_3$ and $q_4$ is methyl. In certain embodiments, $q_1$, $q_2$, $q_3$ and $q_4$ are each H.

In certain embodiments, at least one of $z_1$ and $z_2$ is other than H. In certain embodiments, $z_1$ is fluoro. In certain embodiments, $z_2$ is fluoro. In certain embodiments, $z_1$ and $z_2$ are each fluoro. In certain embodiments, at least one of $z_1$ and $z_2$ is O—$C_1$-$C_6$ alkyl or substituted O—$C_1$-$C_6$ alkyl. In certain embodiments, $z_2$ is O—$C_1$-$C_6$ alkyl or substituted O—$C_1$-$C_6$ alkyl. In certain embodiments, each $z_1$ and $z_2$ is H.

In certain embodiments, oligomeric compounds are provided comprising at least one region of at least 11 contiguous β-D-2'-deoxyribonucleosides and at least one region of from 1 to about 5 contiguous tricyclic nucleosides wherein each tricyclic nucleoside has formula I:

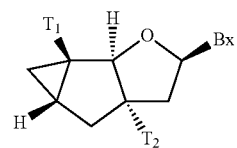

I wherein independently for each of said tricyclic nucleosides having formula I:

Bx is a heterocyclic base moiety;

one of $T_1$ and $T_2$ is an internucleoside linking group attaching said tricyclic nucleoside of formula I to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula I to said oligomeric compound;

and wherein said oligomeric compound comprises from 12 to about 40 linked monomeric subunits and is complementary to at least a portion of a target RNA.

In certain embodiments, oligomeric compounds are provided comprising at least one region of at least 11 contiguous β-D-2'-deoxyribonucleosides and at least one region of from 1 to about 5 contiguous tricyclic nucleosides having formula I wherein said oligomeric compound comprises a 3'-hemimer or a 5'-hemimer.

In certain embodiments, gapped oligomeric compounds are provided comprising two external regions separated by an internal region wherein each external region independently comprises from 1 to 5 contiguous tricyclic nucleosides of formula I and the internal region comprises from 11 to about 23 contiguous monomeric subunits independently selected β-D-ribonucleosides, β-D-2'-deoxyribonucleosides and modified nucleosides.

In certain embodiments, each monomeric subunit in the internal region is a β-D-2'-deoxyribonucleoside or a modified nucleoside. In certain embodiments, each monomeric subunit in the internal region is a β-D-2'-deoxyribonucleoside. In certain embodiments, the internal region comprises from about 11 to about 18 β-D-2'-deoxyribonucleosides. In certain embodiments, the internal region comprises from 11 to about 14 β-D-2'-deoxyribonucleosides. In certain embodiments, the internal region comprises from 12 to about 14 β-D-2'-deoxyribonucleosides.

In certain embodiments, each external region comprises from 1 to 3 tricyclic nucleosides of formula I. In certain embodiments, each external region comprises 2 tricyclic nucleosides of formula I.

In certain embodiments, each Bx is, independently, uracil, 5-methyluracil, thymine, cytosine, 5-methylcytosine, 2,6-diaminopurine, adenine or guanine.

In certain embodiments, the oligomeric compound further comprises a 5' or 3'-terminal group.

In certain embodiments, each linked monomeric subunit that is not a β-D-2'-deoxyribonucleoside or a tricyclic nucleoside having formula II is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, the oligomeric compound comprises a 5'-terminal tricyclic nucleoside of formula II wherein $T_1$ is a 5'-phosphate group.

In certain embodiments, each internucleoside linkage is a phosphodiester. In certain embodiments, each internucleoside linkage is a phosphorothioate. In certain embodiments, each internucleoside linking group is, independently, a phosphodiester or a phosphorothioate. In certain embodiments, each internucleoside linking group is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, gapped oligomeric compounds are provided comprising two external regions separated by an internal region wherein each external region independently comprises from 1 to 5 contiguous tricyclic nucleosides of formula I and the internal region comprises from 11 to about 23 contiguous monomeric subunits independently selected β-D-ribonucleosides, β-D-2'-deoxyribonucleosides and modified nucleosides wherein the oligomeric compound comprises from 11 to about 22 linked monomeric subunits. In certain embodiments, the oligomeric compound comprises from 11 to about 18 linked monomeric subunits. In certain embodiments, the oligomeric compound comprises from 11 to about 14 linked monomeric subunits. In certain embodiments, the oligomeric compound comprises from 12 to about 16 linked monomeric subunits.

The present disclosure provides methods comprising contacting a cell with an oligomeric compound, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula I:

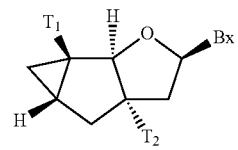

wherein independently for each of said tricyclic nucleosides having formula I:
Bx is a heterocyclic base moiety;
one of $T_1$ and $T_2$ is an internucleoside linking group attaching said tricyclic nucleoside of formula I to said oligomeric compound and the other of $T_1$ and $T_2$ is hydroxyl, a protected hydroxyl, a phosphate moiety, a terminal group, a linked conjugate group or an internucleoside linking group attaching said tricyclic nucleoside of formula I to said oligomeric compound;
wherein said oligomeric compound is complementary to at least a portion of a target RNA; and
wherein said oligomeric compound comprises from about 8 to about 40 linked monomeric subunits.

In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods further comprise evaluating the antisense activity of said oligomeric compound on said cell. In certain embodiments, the evaluating step comprises detecting the levels of target RNA. In certain embodiments, the evaluating step comprises detecting the levels of a protein. In certain embodiments, the evaluating step comprises detection of one or more phenotypic effects.

In certain embodiments, each linked monomeric subunit that is not a β-D-2'-deoxyribonucleoside or a tricyclic nucleoside having formula I is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, the oligomeric compound comprises a blockmer, a 3'-hemimer or 5'-hemimer. In certain embodiments, each monomeric subunit is, independently, a β-D-2'-deoxyribonucleoside or a tricyclic nucleosides having formula I.

The present disclosure also provided methods wherein the oligomeric compound comprises a gapped oligomeric compound comprising two external regions separated by an internal region wherein each external region independently comprises from 1 to 5 contiguous tricyclic nucleosides of formula I and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, each monomeric subunit in the internal region is a β-D-2'-deoxyribonucleoside.

Various gapped oligomeric compounds are amenable to the instant methods. In certain embodiments, the internal region comprises from about 8 to about 12 β-D-2'-deoxyribonucleosides. In certain embodiments, each external region comprises from 1 to 3 tricyclic nucleosides of formula I. In certain embodiments, the internal region comprises from about 10 to about 12 β-D-2'-deoxyribonucleosides. In certain embodiments, the internal region comprises from 11 to about 18 β-D-2'-deoxyribonucleosides. In certain embodiments, each external region comprises from 1 to 3 tricyclic nucleosides of formula I. In certain embodiments, the internal region comprises from 12 to about 14 β-D-2'-deoxyribonucleosides. In certain embodiments, each external region independently comprises from 1 to 3 tricyclic nucleosides of formula I. In certain embodiments, each external region comprises 2 tricyclic nucleosides of formula I. In certain embodiments, the internal region comprises 10 β-D-2'-deoxyribonucleosides. In certain embodiments, the $T_1$ group of the 5'-terminal tricyclic nucleoside is a phosphate group.

In certain embodiments, oligomeric compounds are provided for use in the instant methods wherein each internucleoside linkage is a phosphodiester. In certain embodiments, oligomeric compounds are provided for use in the instant methods wherein each internucleoside linkage is a phosphorothioate. In certain embodiments, oligomeric compounds are provided for use in the instant methods wherein each internucleoside linkage is a phosphorothioate. In certain embodiments, oligomeric compounds are provided for use in the instant methods wherein each internucleoside linking group is, independently, a phosphodiester or a phosphorothioate. In certain embodiments, oligomeric compounds are provided for use in the instant methods wherein each internucleoside linking group is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, oligomeric compounds are provided for use in the instant methods comprising from 8 to about 18 linked monomeric subunits. In certain embodiments, oligomeric compounds are provided for use in the instant methods comprising from 10 to about 16 linked monomeric subunits. In certain embodiments, oligomeric compounds are provided for use in the instant methods comprising from 10 to about 14 linked monomeric subunits. In certain embodiments, oligomeric compounds are provided for use in the instant methods comprising from 17 to about 26 linked monomeric subunits. In certain embodiments, oligomeric compounds are provided for use in the instant methods comprising from 18 to about 21 linked monomeric subunits. In certain embodiments, oligomeric compounds are provided for use in the instant methods comprising from 19 to about 20 linked monomeric subunits.

The present disclosure provides methods comprising administering an oligomeric compound to an animal, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula I:

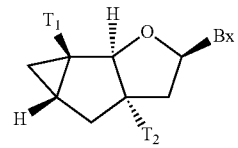

wherein independently for each of said tricyclic nucleosides having formula I:

Bx is a heterocyclic base moiety;

one of $T_1$ and $T_2$ is an internucleoside linking group attaching said tricyclic nucleoside of formula I to said oligomeric compound and the other of $T_1$ and $T_2$ is hydroxyl, a protected hydroxyl, a phosphate moiety, a terminal group, a linked conjugate group or an internucleoside linking group attaching said tricyclic nucleoside of formula I to said oligomeric compound;

wherein said oligomeric compound is complementary to at least a portion of a target RNA; and wherein said oligomeric compound comprises from about 8 to about 40 linked monomeric subunits.

In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods further comprise evaluating the antisense activity of said oligomeric compound on said animal. In certain embodiments, the methods further comprise evaluating comprises detecting the levels of target RNA. In certain embodiments, the step of evaluating comprises detecting the levels of a protein. In certain embodiments, the step of evaluating comprises detection of one or more phenotypic effects.

In certain embodiments, each linked monomeric subunit that is not a β-D-2'-deoxyribonucleoside or a tricyclic nucleoside having formula I is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, the oligomeric compound comprises a blockmer, a 3'-hemimer or 5'-hemimer. In certain embodiments, each monomeric subunit is, independently, a β-D-2'-deoxyribonucleoside or a tricyclic nucleosides having formula I.

The present disclosure also provided methods wherein the oligomeric compound comprises a gapped oligomeric compound comprising two external regions separated by an internal region wherein each external region independently comprises from 1 to 5 contiguous tricyclic nucleosides of formula I and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, each monomeric subunit in the internal region is a β-D-2'-deoxyribonucleoside.

Various gapped oligomeric compounds are amenable to the instant methods. In certain embodiments, the internal region comprises from about 8 to about 12 β-D-2'-deoxyribonucleosides. In certain embodiments, each external region comprises from 1 to 3 tricyclic nucleosides of formula I. In certain embodiments, the internal region comprises from about 10 to about 12 β-D-2'-deoxyribonucleosides. In certain embodiments, the internal region comprises from 11 to about 18 β-D-2'-deoxyribonucleosides. In certain embodiments, each external region comprises from 1 to 3 tricyclic nucleosides of formula I. In certain embodiments, the internal region comprises from 12 to about 14 β-D-2'-deoxyribonucleosides. In certain embodiments, each external region independently comprises from 1 to 3 tricyclic nucleosides of formula I. In certain embodiments, each external region comprises 2 tricyclic nucleosides of formula I. In certain embodiments, the internal region comprises 10 β-D-2'-deoxyribonucleosides. In certain embodiments, the $T_1$ group of the 5'-terminal tricyclic nucleoside is a phosphate group.

In certain embodiments, oligomeric compounds are provided for use in the instant methods wherein each internucleoside linkage is a phosphodiester. In certain embodiments, oligomeric compounds are provided for use in the instant methods wherein each internucleoside linkage is a phosphorothioate. In certain embodiments, oligomeric compounds are provided for use in the instant methods wherein each internucleoside linkage is a phosphorothioate. In certain embodiments, oligomeric compounds are provided for use in the instant methods wherein each internucleoside linking group is, independently, a phosphodiester or a phosphorothioate. In certain embodiments, oligomeric compounds are provided for use in the instant methods wherein each internucleoside linking group is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, oligomeric compounds are provided for use in the instant methods comprising from 8 to about 18 linked monomeric subunits. In certain embodiments, oligomeric compounds are provided for use in the instant methods comprising from 10 to about 16 linked monomeric subunits. In certain embodiments, oligomeric compounds are provided for use in the instant methods comprising from 10 to about 14 linked monomeric subunits. In certain embodiments, oligomeric compounds are provided for use in the instant methods comprising from 17 to about 26 linked monomeric subunits. In certain embodiments, oligomeric compounds are provided for use in the instant methods comprising from 18 to about 21 linked monomeric subunits. In certain embodiments, oligomeric compounds are provided for use in the instant methods comprising from 19 to about 20 linked monomeric subunits.

The present disclosure provides oligomeric compounds wherein each oligomeric compound comprises at least one region of at least 2 contiguous β-D-2'-deoxyribonucleosides and at least one region of from 1 to about 5 contiguous tricyclic nucleosides wherein each tricyclic nucleoside has formula I:

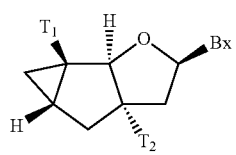

I wherein independently for each of said tricyclic nucleosides having formula I:
Bx is a heterocyclic base moiety;
one of $T_1$ and $T_2$ is an internucleoside linking group attaching said tricyclic nucleoside of formula I to said oligomeric compound and the other of $T_1$ and $T_2$ is hydroxyl, a protected hydroxyl, a phosphate moiety, a terminal group, a linked conjugate group or an internucleoside linking group attaching said tricyclic nucleoside of formula I to said oligomeric compound;
the internucleoside linkages between β-D-2'-deoxyribonucleosides in the at least one region of at least 2 contiguous β-D-2'-deoxyribonucleosides are each a phosphorothioate; and
wherein said oligomeric compound comprises from about 8 to about 40 linked monomeric subunits.

In certain embodiments, each linked monomeric subunit that is not a β-D-2'-deoxyribonucleoside or a tricyclic nucleoside having formula I is a modified nucleoside. In certain embodiments, each modified nucleoside is, independently, a bicyclic modified nucleoside, a 2'-modified nucleoside, a 4'-thio modified nucleoside or a 4'-thio-2'-modified nucleoside.

In certain embodiments, the oligomeric compound comprises a blockmer, a 3'-hemimer or 5'-hemimer. In certain embodiments, each monomeric subunit is, independently, a β-D-2'-deoxyribonucleoside or a tricyclic nucleosides having formula I.

The present disclosure also provided methods wherein the oligomeric compound comprises a gapped oligomeric compound comprising two external regions separated by an internal region wherein each external region independently comprises from 1 to 5 contiguous tricyclic nucleosides of formula I and the internal region comprises from 6 to about 23 contiguous monomeric subunits independently selected from nucleosides and modified nucleosides. In certain embodiments, each monomeric subunit in the internal region is, independently, a β-D-2'-deoxyribonucleoside or a modified nucleoside. In certain embodiments, each monomeric subunit in the internal region is a β-D-2'-deoxyribonucleoside.

Various gapped oligomeric compounds are amenable to the instant methods. In certain embodiments, the internal region comprises from about 8 to about 12 β-D-2'-deoxyribonucleosides. In certain embodiments, each external region comprises from 1 to 3 tricyclic nucleosides of formula I. In certain embodiments, the internal region comprises from about 10 to about 12 β-D-2'-deoxyribonucleosides. In certain embodiments, the internal region comprises from 11 to about 18 β-D-2'-deoxyribonucleosides. In certain embodiments, each external region comprises from 1 to 3 tricyclic nucleosides of formula I. In certain embodiments, the internal region comprises from 12 to about 14 β-D-2'-deoxyribonucleosides. In certain embodiments, each external region independently comprises from 1 to 3 tricyclic nucleosides of formula I. In certain embodiments, each external region comprises 2 tricyclic nucleosides of formula I. In certain embodiments, the internal region comprises 10 β-D-2'-deoxyribonucleosides. In certain embodiments, the $T_1$ group of the 5'-terminal tricyclic nucleoside is a phosphate group.

In certain embodiments, oligomeric compounds are provided for use in the instant methods wherein each internucleoside linkage that is not a phosphorothioate is a phosphodiester. In certain embodiments, oligomeric compounds are provided for use in the instant methods wherein each internucleoside linkage is a phosphorothioate. In certain embodiments, gapped oligomeric compounds are provided for use in the instant methods wherein each internucleoside linkage is a phosphorothioate. In certain embodiments, oligomeric compounds are provided for use in the instant methods wherein each internucleoside linking group that is not a phosphorothioate is, independently, a phosphodiester or a phosphorothioate. In certain embodiments, oligomeric compounds are provided for use in the instant methods wherein each internucleoside linking group that is not a phosphorothioate is, independently, a phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate or a boranophosphate.

In certain embodiments, oligomeric compounds are provided for use in the instant methods comprising from 8 to about 18 linked monomeric subunits. In certain embodiments, oligomeric compounds are provided for use in the instant methods comprising from 10 to about 16 linked monomeric subunits. In certain embodiments, oligomeric compounds are provided for use in the instant methods comprising from 10 to about 14 linked monomeric subunits. In certain embodiments, oligomeric compounds are provided for use in the instant methods comprising from 17 to about 26 linked monomeric subunits. In certain embodiments, oligomeric compounds are provided for use in the instant methods comprising from 18 to about 21 linked monomeric subunits. In certain embodiments, oligomeric compounds are provided for use in the instant methods comprising from 19 to about 20 linked monomeric subunits.

DETAILED DESCRIPTION OF THE INVENTION

The present disclosure provides tricyclic nucleosides, oligomeric compounds comprising the tricyclic nucleosides and methods of using the oligomeric compounds. More particularly, the present disclosure provides oligomeric compounds having at least one region of at least from one to about 5 tricyclic nucleosides as provided herein and at least one region of at least 2 contiguous β-D-2'-deoxyribonucleosides. The present disclosure further provides methods comprising contacting a cell with at least one of the oligomeric compounds. The present disclosure also provides methods comprising administering at least one of the oligomeric compounds to an animal. In certain embodiments, the oligomeric compounds hybridize to a portion of a target RNA resulting in loss of normal function of the target RNA.

In certain embodiments, methods are provided comprising contacting a cell with an oligomeric compound, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula II:

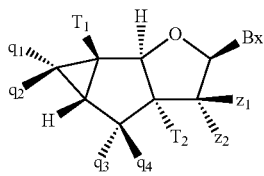

wherein independently for each of said tricyclic nucleosides having formula II:
Bx is a heterocyclic base moiety;
one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, O—$N(E_1)(E_2)$, C(=O)$N(E_1)(E_2)$, C(=O)—N$(E_3)$-$(CH_2)_r$—$N(E_1)(E_2)$ and $CH_2$—N(H)—C(=$NE_3$)[N$(E_1)(E_2)$] wherein each $E_1$, $E_2$ and $E_3$ is, independently, H, $C_1$-$C_6$ alkyl or a protecting group and r is from 2 to about 6; and wherein said oligomeric compound comprises from about 8 to about 40 linked monomeric subunits and is complementary to at least a portion of a target RNA.

In certain embodiments, the contacting step is performed on a cell or group of cells. In certain embodiments, the cells are in an animal. In a preferred embodiment, the cells are in a human.

In certain embodiments, methods are provided comprising administering an oligomeric compound to an animal, wherein said oligomeric compound comprises at least one region of at least 2 contiguous β-D-2'-deoxyribonucleosides and at least one region of from 1 to about 5 contiguous tricyclic nucleosides wherein each tricyclic nucleoside has formula II:

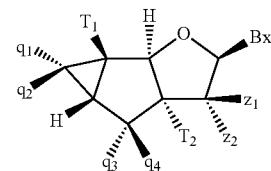

wherein independently for each of said tricyclic nucleosides having formula II:
Bx is a heterocyclic base moiety;
one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, O—$C_1$-$C_6$ alkyl, O—$C_2$-$C_6$ alkenyl, O—$C_2$-$C_6$ alkynyl, substituted $C_1$-$C_6$ alkyl, substituted O—$C_1$-$C_6$ alkyl, substituted O—$C_2$-$C_6$ alkenyl or substituted O—$C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, $O-N(E_1)(E_2)$, $C(=O)N(E_1)(E_2)$, $C(=O)-N(E_3)-(CH_2)_r-N(E_1)(E_2)$ and $CH_2-N(H)-C(=NE_3)[N(E_1)(E_2)]$ wherein each $E_1$, $E_2$ and $E_3$ is, independently, H, $C_1$-$C_6$ alkyl or a protecting group and r is from 2 to about 6; and wherein said oligomeric compound comprises from about 8 to about 40 linked monomeric subunits and is complementary to at least a portion of a target RNA.

In one embodiment, the target RNA is selected from mRNA, pre-mRNA and micro RNA. A preferred target RNA is mRNA with human mRNA being more preferred.

The present methods can be evaluated using methods that are known in the art. One particular method of evaluating the methods is to evaluate the antisense activity of the oligomeric compounds on a cell, a group of cells or in an animal. Preferred animals for evaluating the antisense activity of the oligomeric compounds are mammals with humans being more preferred.

Another method of evaluating the activity of the oligomeric compounds is to monitor the levels of target RNA or one or more proteins affected by a change in target RNA concentration. Phenotypic effects can also be monitored.

In certain embodiments, oligomeric compounds are provided comprising at least one tricyclic nucleoside has formula I:

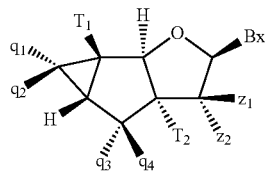

wherein independently for each of said tricyclic nucleosides having formula II:

Bx is a heterocyclic base moiety;

one of $T_1$ and $T_2$ is an internucleoside linking group attaching said tricyclic nucleoside of formula II to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula II to said oligomeric compound;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, $O-C_1$-$C_6$ alkyl, $O-C_2$-$C_6$ alkenyl, $O-C_2$-$C_6$ alkynyl, substituted $C_1$-$C_6$ alkyl, substituted $O-C_1$-$C_6$ alkyl, substituted $O-C_2$-$C_6$ alkenyl or substituted $O-C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, $O-N(E_1)(E_2)$, $C(=O)N(E_1)(E_2)$, $C(=O)-N(E_3)-(CH_2)_r-N(E_1)(E_2)$ and $CH_2-N(H)-C(=NE_3)[N(E_1)(E_2)]$ wherein each $E_1$, $E_2$ and $E_3$ is, independently, H, $C_1$-$C_6$ alkyl or a protecting group and r is from 2 to about 6; and wherein said oligomeric compound comprises from about 8 to about 40 linked monomeric subunits and is complementary to at least a portion of a target RNA; and wherein at least one of $q_1$, $q_2$, $q_3$, $q_4$, $z_1$ and $z_2$ is other than H.

In certain embodiments, oligomeric compounds are provided comprising at least one region of at least 11 contiguous β-D-2'-deoxyribonucleosides and at least one region of from 1 to about 5 contiguous tricyclic nucleosides wherein each tricyclic nucleoside has formula I:

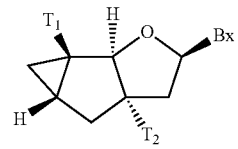

wherein independently for each of said tricyclic nucleosides having formula I:

Bx is a heterocyclic base moiety;

one of $T_1$ and $T_2$ is an internucleoside linking group attaching said tricyclic nucleoside of formula I to said oligomeric compound and the other of $T_1$ and $T_2$ is hydroxyl, a protected hydroxyl, a phosphate moiety, a 5' or 3'-terminal group or an internucleoside linking group attaching said tricyclic nucleoside of formula I to said oligomeric compound;

and wherein said oligomeric compound comprises from 12 to about 40 linked monomeric subunits and is complementary to at least a portion of a target RNA.

In certain embodiments tricyclic nucleosides are provided having formula III:

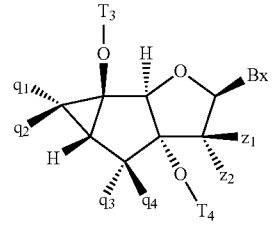

wherein:

Bx is a heterocyclic base moiety;

one of $T_3$ and $T_4$ is H or a hydroxyl protecting group and the other of $T_3$ and $T_4$ is H, a hydroxyl protecting group or a reactive phosphorus group;

$q_1$, $q_2$, $q_3$ and $q_4$ are each, independently, H, halogen, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

$z_1$ and $z_2$ are each, independently, H, halogen, $C_1$-$C_6$ alkyl, $O-C_1$-$C_6$ alkyl, $O-C_2$-$C_6$ alkenyl, $O-C_2$-$C_6$ alkynyl, substituted $C_1$-$C_6$ alkyl, substituted $O-C_1$-$C_6$ alkyl, substituted $O-C_2$-$C_6$ alkenyl or substituted $O-C_2$-$C_6$ alkynyl;

wherein each substituted group is, independently, mono or poly substituted with optionally protected substituent groups independently selected from halogen, oxo, $N_3$, CN, $OE_1$, $N(E_1)(E_2)$, $O-N(E_1)(E_2)$, $C(=O)N(E_1)(E_2)$, $C(=O)-N$ ($E_3$)-($CH_2$)$_r$—N($E_1$)($E_2$) and $CH_2$—N(H)—C(=N$E_3$)[N($E_1$)($E_2$)] wherein each $E_1$, $E_2$ and $E_3$ is, independently, H, $C_1$-$C_6$ alkyl or a protecting group and r is from 2 to about 6; and wherein at least one of $q_1$, $q_2$, $q_3$, $q_4$, $z_1$ and $z_2$ is other than H.

In certain embodiments, the oligomeric compounds comprising one or more of the tricyclic nucleosides as provided herein can be described as having a particular motif Motifs amenable to the present disclosure include but are not limited to a gapped motif, a hemimer motif, a blockmer motif, a fully modified motif, a positionally modified motif and an alternating motif. In conjunction with these motifs a wide variety of linkages can also be used including but not limited to phosphodiester and phosphorothioate linkages used uniformly or in combinations. The positioning of the tricyclic nucleosides as provided herein in combination with the use of linkage strategies can be optimized to enhance activity for a selected target. Such motifs can be further modified by the inclusion of 5' or 3'-terminal groups that are routinely attached at the terminal 3', 5' or equivalent position ($T_1$ or $T_2$ of the tricyclic nucleosides as provided herein) including but not limited to further modified or unmodified nucleosides, conjugate groups and phosphate moieties. Modified or unmodified nucleosides used as terminal groups can be hybridizing or non-hybridizing relative to a nucleic acid target or a second strand in a double stranded composition.

The term "motif" refers to the distribution of sugar modified nucleosides within an oligomeric compound relative to other sugar modified nucleosides and or unmodified nucleosides. For defining motifs, the tricyclic nucleosides as provided herein can also be considered sugar modified nucleosides. The pattern is defined by the positioning of one type of sugar modified nucleosides relative to the positioning of other sugar modified nucleosides and/or unmodified nucleosides (β-D-ribonucleosides and/or β-D-deoxyribonucleosides). More specifically, the motif of a particular oligomeric compound is determined by the positioning of different sugar groups relative to each other. The type of heterocyclic base and internucleoside linkages used at each position is variable and is not a factor in determining the motif of an oligomeric compound. The presence of one or more other groups including terminal groups, protecting groups or capping groups is also not a factor in determining the motif.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used in the present disclosure the term "gapmer" or "gapped oligomeric compound" is meant to include a contiguous sequence of linked monomeric subunits divided into 3 regions, an internal region having an external region on each of the 5' and 3' ends. The external regions are differentiated from the internal region by at least having different sugar groups comprising the monomeric subunits. The present disclosure includes gapmers wherein essentially each monomeric subunit in the external regions is a tricyclic nucleoside as provided herein and each monomeric subunit in the internal region is a β-D-ribonucleoside, β-D-2'-deoxyribonucleoside or a modified nucleoside. Each of the regions of a gapped oligomeric compound is essentially uniformly modified e.g. the sugar groups are identical with at least the internal region having different sugar groups than each of the external regions. The internal region or the gap generally comprises β-D-2'-deoxyribonucleosides but can be a sequence of sugar modified nucleosides or β-D-ribonucleosides. A preferred gapped oligomeric compound according to the present disclosure comprises an internal region of β-D2'-deoxyribonucleosides with both of the external regions comprising tricyclic nucleosides as provided herein.

In one aspect of the present disclosure, gapped oligomeric compounds are provided comprising one or two tricyclic nucleosides as provided herein at the 5'-end, two or three tricyclic nucleosides as provided herein at the 3'-end and an internal region of from 10 to 16 nucleosides. In one aspect of the present disclosure, gapped oligomeric compounds are provided comprising one tricyclic nucleoside as provided herein at the 5'-end, two tricyclic nucleosides as provided herein at the 3'-end and an internal region of from 10 to 16 nucleosides. In one aspect of the present disclosure, gapped oligomeric compounds are provided comprising one tricyclic nucleoside as provided herein at the 5'-end, two tricyclic nucleosides as provided herein at the 3'-end and an internal region of from 10 to 14 nucleosides. In one aspect of the present disclosure, gapped oligomeric compounds are provided comprising two tricyclic nucleosides as provided herein at the 5'-end, two tricyclic nucleosides as provided herein at the 3'-end and an internal region of from 10 to 16 nucleosides. In one aspect of the present disclosure, the internal region is essentially a contiguous sequence of β-D-deoxyribonucleosides. In one aspect of the present disclosure, oligomeric compounds are provided that further include one or more 5'- and/or 3'-terminal groups including but not limited to further modified or unmodified nucleosides, conjugate groups, phosphate moieties and other useful groups known to the art skilled.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—N$R_{bb}$$R_{cc}$), imino(=N$R_{bb}$), amido (—C(O)N—$R_{bb}$$R_{cc}$ or —N($R_{bb}$)C(O)$R_{aa}$), azido (—$N_3$), nitro (—$NO_2$), cyano (—CN), carbamido (—OC(O)N$R_{bb}$$R_{cc}$ or —N($R_{bb}$)C(O)O$R_{aa}$), ureido (—N($R_{bb}$)C(O)N$R_{bb}$$R_{cc}$), thioureido (—N($R_{bb}$)C(S)N$R_{bb}$$R_{cc}$), guanidinyl (—N($R_{bb}$)—C(=N$R_{bb}$)N$R_{bb}$$R_{cc}$), amidinyl (—C(=N$R_{bb}$)N$R_{bb}$$R_{cc}$ or —N($R_{bb}$)C(N$R_{bb}$)$R_{aa}$), thiol (—S$R_{bb}$), sulfinyl (—S(O)$R_{bb}$), sulfonyl (—S(O)$_2$$R_{bb}$), sulfonamidyl (—S(O)$_2$N$R_{bb}$$R_{cc}$ or —N($R_{bb}$)S(O)$_2$$R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used in the present disclosure includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "oxo" refers to the group (=O).

The terms "bicyclic nucleic acid (BNA)" and "bicyclic nucleoside" as used in the present disclosure includes nucleosides wherein the furanose ring includes a bridge connecting two of the ring's non-geminal carbon atoms, thereby forming a bicyclic ring system. In a broader sense the terms include any bicyclic monomer that can be placed into an oligomeric compound that will not inhibit duplex formation and will hybridize to a nucleoside in a target or complementary strand.

Linking groups or bifunctional linking moieties such as those known in the art are amenable to the present disclosure. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a non-limiting list of preferred substituent groups includes hydroxyl, amino, alkoxy, carboxy, benzyl, phenyl, nitro, thiol, thioalkoxy, halogen, alkyl, aryl, alkenyl and alkynyl.

In one aspect of the present disclosure oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "5-terminal group" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (a group for enhancing uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy) ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, 6-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

The term "orthogonally protected" refers to functional groups which are protected with different classes of protecting groups, wherein each class of protecting group can be removed in any order and in the presence of all other classes (see, Barany, G. and Merrifield, R. B., J. Am. Chem. Soc., 1977, 99, 7363; idem, 1980, 102, 3084.) Orthogonal protection is widely used in for example automated oligonucleotide synthesis. A functional group is deblocked in the presence of one or more other protected functional groups which are not affected by the deblocking procedure. This deblocked functional group is reacted in some manner and at some point a further orthogonal protecting group is removed under a different set of reaction conditions. This allows for selective chemistry to arrive at a desired compound or oligomeric compound.

The present disclosure provides compounds having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidite ($P^{III}$ chemistry) as reactive phosphites. The intermediate phosphite compounds are subsequently oxidized to the $P^V$ state using known methods to yield, in preferred embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

In one aspect of the present disclosure, oligomeric compounds are provided having at least one non-naturally occurring internucleoside linkage. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,306; 5,550,111; 5,563,253; 5,571, 799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In the context of this invention, the term "oligonucleoside" refers to a sequence of nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein may contain one or more asymmetric centers allowing enantiomers, diastereomers, and other stereoisomeric forms that may be defined, in terms of absolute stereochemistry, as (R)- or (S)-, α or β, or as (D)- or (L)- such as for amino acids. The present disclosure is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In the context of the present disclosure, the term "oligomeric compound" refers to a polymer having at least a region that is capable of hybridizing to a nucleic acid molecule. The term "oligomeric compound" includes oligonucleotides, oligonucleotide analogs and oligonucleosides as well as mixed polymers comprising nucleic acid and non-nucleic acid components such as nucleotide mimetics, and chimeric oligomeric compounds comprising mixtures of monomeric subunits from any of these categories. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as a peptide nucleic acid monomer. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The term "nucleobase" or "heterocyclic base moiety" as used herein, is intended to by synonymous with "nucleic acid base or mimetic thereof" In general, a nucleobase or heterocyclic base moiety is any substructure that contains one or more atoms or groups of atoms capable of hydrogen bonding to a base of a nucleic acid.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more modified or non-naturally occurring portions. Such modified or non-naturally occurring oligonucleotides are often desired over naturally occurring forms because of desirable properties such as, for example, enhanced cellular uptake, enhanced affinity for nucleic acid target and increased stability in the presence of nucleases.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosine's, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,750,692; 5,830,653; 5,763,588; 6,005,096; and 5,681,941, certain of which are commonly owned with the instant application, and each of which is herein incorporated by reference.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [C(R)$_2$] or a heteroatom or substituted heteroatom (NR). Modified sugar moieties can also comprise mixtures of these modifications such as for example putting a 5'-substituent group on a bicyclic nucleoside.

Examples of substituent groups useful for modifying sugar moieties of nucleosides include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$, 2'-O(CH$_2$)$_2$SCH$_3$, 2'-O—CH$_2$—CH=CH$_2$(MOE), 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)], 5'-vinyl, 5'-methyl (R or S) and 4'-S wherein each R$_m$ and R$_n$ is, independently, H, substituted or unsubstituted C$_1$-C$_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'- C—H(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

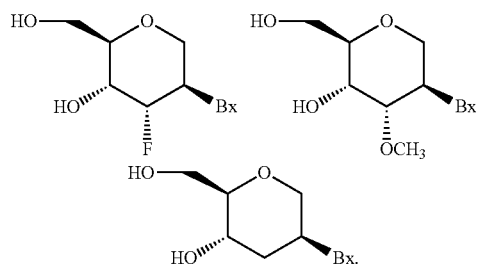

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Each of the oligomeric compounds of the present disclosure comprises a continuous sequence of linked monomeric subunits wherein at least one of the monomeric subunits is a tricyclic nucleoside as provided herein. In one aspect, each monomeric subunit that is not a tricyclic nucleoside as provided herein is independently a nucleoside or a modified nucleoside (sugar modified nucleoside, base modified nucleoside, sugar and base modified nucleoside). In another aspect, each monomeric subunit that is not a tricyclic nucleoside as provided herein is independently any monomeric subunit that can hybridize a nucleoside in a second or target strand, an abasic nucleoside, a nucleoside (DNA or RNA), a sugar modified nucleoside, a base modified nucleoside, a sugar and base modified nucleoside, a nucleoside mimic or a nucleoside surrogate.

The oligomeric compounds in accordance with the present disclosure can comprise from about 8 to about 80 monomeric subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomeric subunits in length or any range therewithin.

In another embodiment, the oligomeric compounds of the invention are 8 to 40 monomeric subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomeric subunits in length or any range therewithin.

In another embodiment, the oligomeric compounds of the invention are 8 to 20 monomeric subunits in length. One having ordinary skill in the art will appreciate that this embodies oligomeric compounds of 8, 9, 10, 11, 12, 13, 14, 15, 16, 17, 18, 19 or 20 monomeric subunits in length or any range therewithin.

In another embodiment, the oligomeric compounds of the invention are 12 to 23 monomeric subunits in length. One having ordinary skill in the art will appreciate that this embodies oligomeric compounds of 12, 13, 14, 15, 16, 17, 18, 19, 20, 21, 22 or 23 monomeric subunits in length or any range therewithin.

In another embodiment, the oligomeric compounds of the invention are 10 to 16 monomeric subunits in length. One having ordinary skill in the art will appreciate that this embodies oligomeric compounds of 10, 11, 12, 13, 14, 15 or 16 monomeric subunits in length or any range therewithin.

In another embodiment, the oligomeric compounds of the invention are 12 to 16 monomeric subunits in length. One having ordinary skill in the art will appreciate that this embodies oligomeric compounds of 12, 13, 14, 15 or 16 monomeric subunits in length or any range therewithin.

In another embodiment, the oligomeric compounds of the invention are 12 to 14 monomeric subunits in length. One having ordinary skill in the art will appreciate that this embodies oligomeric compounds of 12, 13, 14, 15 or 16 monomeric subunits in length or any range therewithin.

In another embodiment, the oligomeric compounds of the invention are 10 to 14 monomeric subunits in length. One having ordinary skill in the art will appreciate that this embodies oligomeric compounds of 10, 11, 12, 13 or 14 monomeric subunits in length or any range therewithin.

In certain embodiments, the present disclosure provides oligomeric compounds of any of a variety of ranges of lengths of linked monomeric subunits. In certain embodiments, the invention provides oligomeric compounds consisting of X-Y linked monomeric subunits wherein X and Y are each independently, selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9- 12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomeric subunits.

Preferred ranges for the length of the oligomeric compounds in accordance with the present disclosure are 8-16, 8-40, 10-12, 10-14, 10-16, 10-18, 10-20, 10-21, 12-14, 12-16, 12-18, 12-20 and 12-24 linked monomeric subunits.

More preferred ranges for the length of the oligomeric compounds in accordance with the present disclosure are 10-22, 10-18, 12-18, 13-28, 13-24, 14-20, 8-29, 10-27, 13-14, 8-18, 17-26, 18-21 and 19-20 linked monomeric subunits.

In one aspect of the present disclosure gapped oligomeric compounds are provided having external regions comprising from 1 to about 5 contiguous tricyclic nucleosides as provided herein and an internal region comprising from 6 to about 23 contiguous monomeric subunits independently selected from nucleosides and modified nucleosides. Replacing one of the tricyclic nucleosides in the wings with a nucleoside or modified nucleoside is amenable to the present disclosure. In one aspect the internal region comprises from about 8 to about 12 β-D-2'-deoxyribonucleosides. In one aspect the internal region comprises from about 8 to about 12 β-D-2'-deoxyribonucleosides and each external region comprises from 1 to 3 tricyclic nucleosides as provided herein. In one aspect the internal region comprises from about 10 to about 12 β-D-2'-deoxyribonucleosides and each external region comprises from 1 to 3 tricyclic nucleosides as provided herein. In one aspect the internal region comprises from 11 to about 18 β-D-2'-deoxyribonucleosides. In one aspect the internal region comprises from 11 to about 18 β-D-2'-deoxyribonucleosides and each external region comprises from 1 to 3 tricyclic nucleosides as provided herein. In one aspect the internal region comprises from 12 to about 14 β-D-2'-deoxyribonucleosides and each external region comprises from 1 to 3 tricyclic nucleosides as provided herein. In one aspect each external region independently comprises from 1 to 3 tricyclic nucleosides as provided herein. In one aspect each external region independently comprises 2 tricyclic nucleosides as provided herein. In one aspect each external region independently comprises 2 tricyclic nucleosides as provided herein and the internal region comprises 10 β-D-2'-deoxyribonucleosides.

In one aspect of the present disclosure, the preparation of oligomeric compounds is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—Si$(iPr)_3$ (TOM), and the 5'-O-silyl ether-2'-ACE (5'-O-bis (trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present disclosure.

The primary groups being used for commercial RNA synthesis are:
TBDMS=5'-O-DMT-2'-O-t-butyldimethylsilyl;
TOM=2'-O-[(triisopropylsilyl)oxy]methyl;

FPMP=5'-O-DMT-2'-O-[1(2-fluorophenyl)-4-methoxypiperidin-4-yl]; and

DOD/ACE=(5'-O-bis(trimethylsiloxy)cyclododecyloxysilyl ether-2'-O-bis(2-acetoxyethoxy)methyl.

All of the aforementioned RNA synthesis strategies are amenable to the present disclosure. Strategies that would be a hybrid of the above e.g. using a 5'-protecting group from one strategy with a 2'-O-protecting from another strategy is also amenable to the present disclosure.

In the context of this invention, "hybridization" means pairing of complementary strands which includes pairs of oligomeric compounds or an oligomeric compound and a target nucleic acid such as a mRNA. In the present disclosure, one mechanism of pairing involves hydrogen bonding, which may be Watson-Crick, Hoogsteen or reversed Hoogsteen hydrogen bonding, between complementary heterocyclic bases. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds of the present disclosure can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present disclosure. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included in the present disclosure are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present disclosure.

The suitable target segments of the present disclosure may also be combined with their respective complementary antisense oligomeric compounds of the present disclosure to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

In one aspect of the present disclosure oligomeric compounds are used as antisense compounds. As used herein, "antisense compound" refers to an oligomeric compound that is at least partially complementary to a target nucleic acid molecule to which it hybridizes. In certain embodiments, an antisense compound modulates (increases or decreases) expression or amount of a target nucleic acid. In certain embodiments, an antisense compound alters splicing of a target pre-mRNA resulting in a different splice variant. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids.

As used herein, "target RNA" refers to any RNA molecule the expression or activity of which is capable of being modulated by an antisense compound. Target RNAs include, but are not limited to, RNA (including, but not limited to pre-mRNA and mRNA or portions thereof) transcribed from DNA encoding a target protein and miRNA. For example, the target RNA can be a mRNA transcribed from a gene whose expression is associated with a particular disorder or disease state, or a nucleic acid molecule from an infectious agent.

As used herein, "target mRNA" refers to a pre-selected RNA molecule that encodes a protein.

As used herein, "target pre-mRNA" refers to a pre-selected RNA transcript that has not been fully processed into mRNA. Notably, pre-RNA includes one or more intron.

As used herein, "target microRNA" refers to a pre-selected non-coding RNA molecule about 18-30 nucleobases in length that modulates expression of one or more proteins.

As used herein, "target pdRNA" refers to refers to a pre-selected RNA molecule that interacts with one or more promoter to modulate transcription.

As used herein, "target non-coding RNA" refers to a pre-selected RNA molecule that is not translated to generate a protein. Certain non-coding RNAs are involved in regulation of expression.

As used herein, "targeting" or "targeted to" refers to the association of an antisense compound to a particular target nucleic acid molecule or a particular region of nucleotides within a target nucleic acid molecule.

The oligomeric compounds of the present disclosure can also be applied in the areas of drug discovery and target validation. The present disclosure comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present disclosure, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds of the present disclosure can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds of the present disclosure, either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-

11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96 ™ well plate attached to a QIAVAC™ manifold fitted with a waste collection tray and attached to a vacuum source. Vacuum is applied for 1 minute. 500 µL of Buffer RW1 is added to each well of the RNEASY 96 ™ plate and incubated for 15 minutes and the vacuum is again applied for 1 minute. An additional 500 µL of Buffer RW1 is added to each well of the RNEASY 96 ™ plate and the vacuum is applied for 2 minutes. 1 mL of Buffer RPE is then added to each well of the RNEASY 96 ™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                      (SEQ ID NO: 2)
Forward primer: AATGGCTAAGTGAAGATGACAATCAT (SEQ ID NO: 3)
Reverse primer: TGCACATATCATTACACCAGTTCGT
```

And the

```
PCR probe:
                                      (SEQ ID NO: 4)
FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 10

Compound 1 is prepared as per the procedures illustrated in Albeck, N., *Nucleosides, Nucleotides and Nucleic Acids*, 3003, 22, 723-725.
Example 14
Preparation of Compound 17
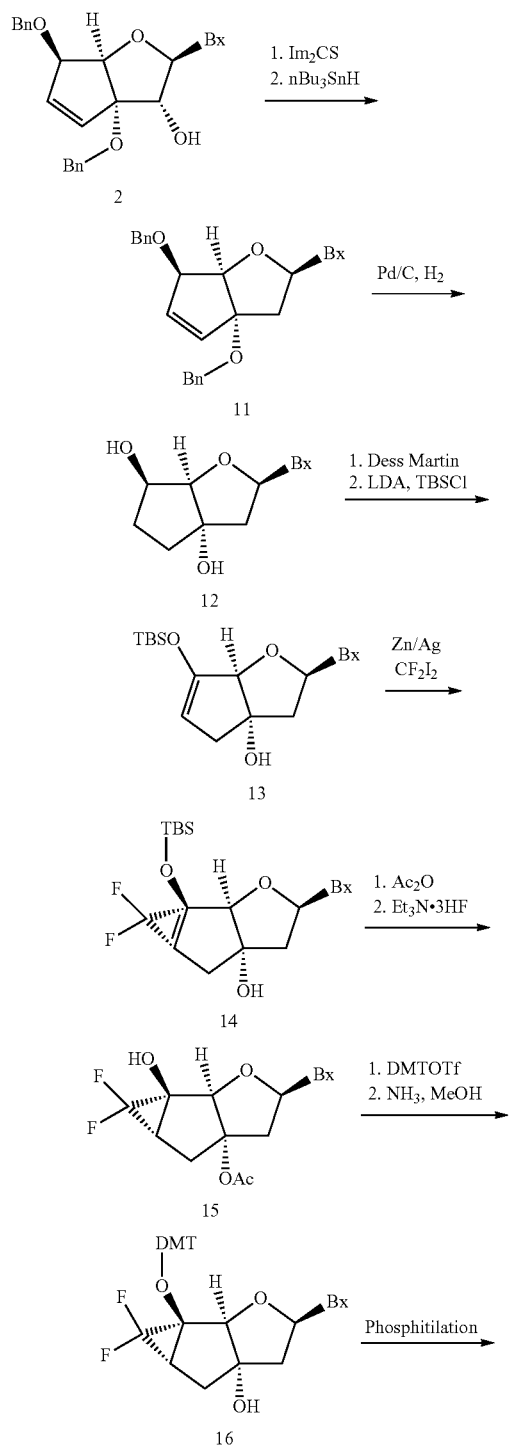
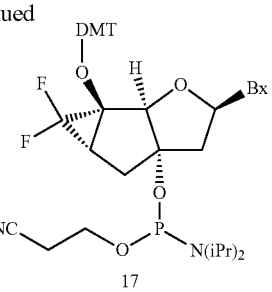
Compound 2 is prepared as per the procedures illustrated in Example 13.
Example 15
Preparation of Compound 21
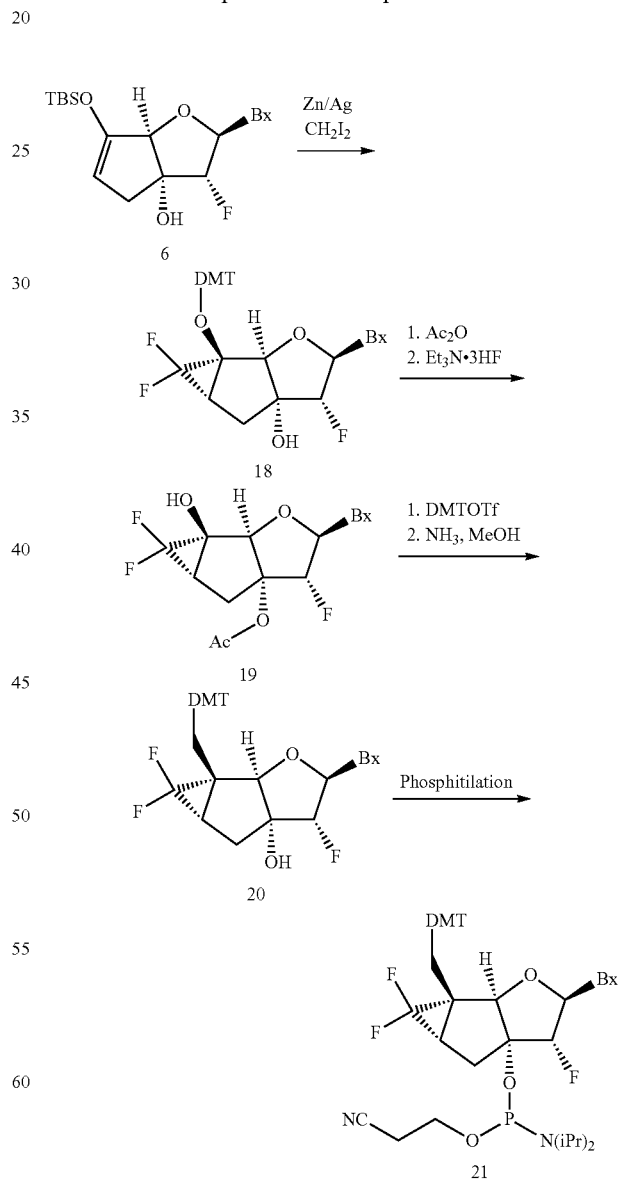
Compound 6 is prepared as per the procedures illustrated in Example 13.

Example 16
Preparation of Compound 30
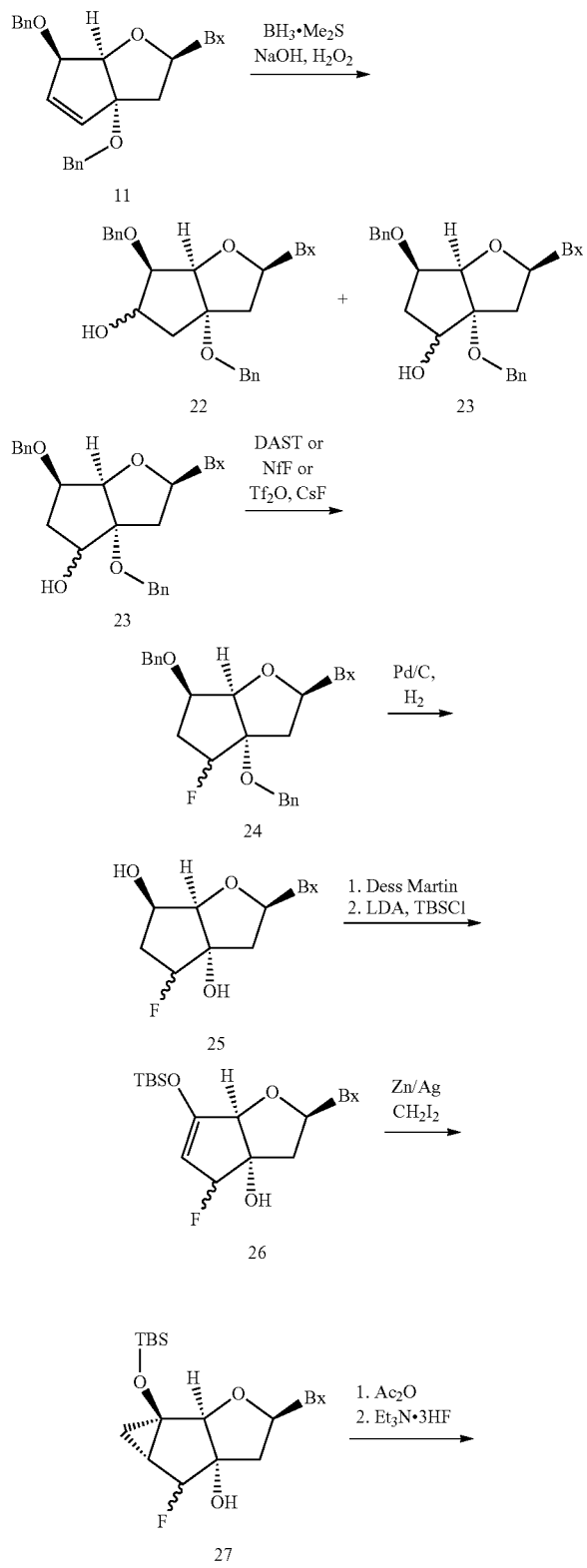
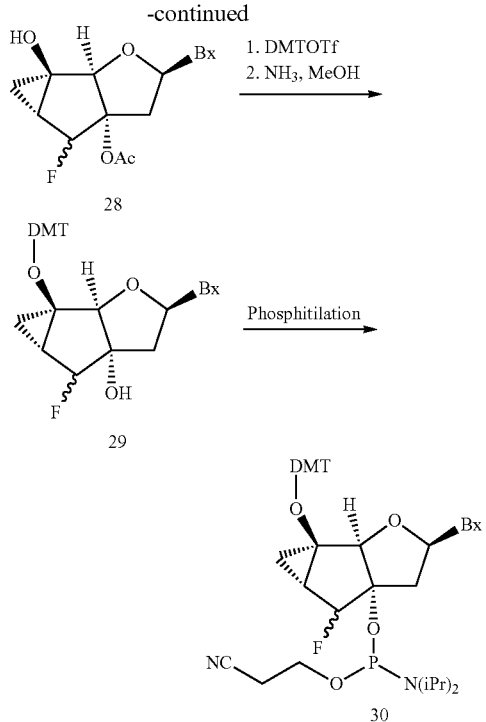
Compound 6 is prepared as per the procedures illustrated in Example 14.
Example 17
Preparation of Compound 37
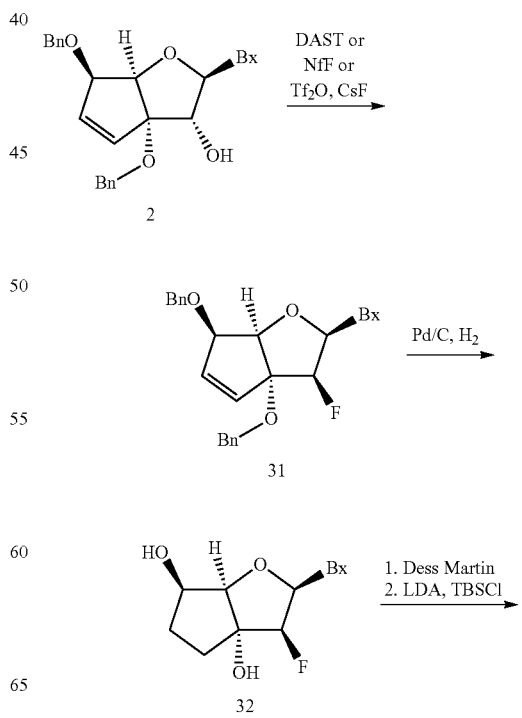

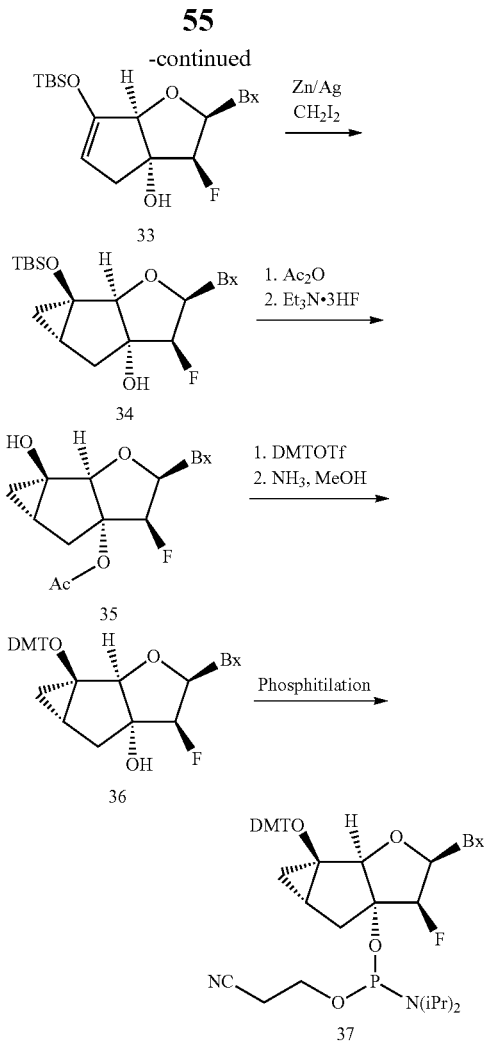

Compound 2 is prepared as per the procedures illustrated in Example 13. Compound 2 is N₃-BOM protected For thymine and uracil heterocyclic bases.

Example 18

Synthesis of Oligonucleotides Having Tricyclic Nucleosides

In general standard phosphoramidites were used for incorporation of dA, T, dG, and dC residues with the synthesis carried out on commercially available solid supports. The phosphoramidites were prepared as a 0.12 M solutions in anhydrous acetonitrile for use in synthesis. The 5'-terminus was phosphorylated using a commercially available phosphorylating reagent (Glen Research Inc., Virginia, USA). The modified oligonucleotide was synthesized on universal solid support (see: Guzaev, et al., *J. Am. Chem. Soc.*, 2003, 125, 2380-2381) using an automated solid phase DNA synthesizer. The phosphoramidites (4 mole eq. solutions) were added with a 12 minute coupling wait time. All other steps in the protocol supplied by the manufacturer were used without modification. A solution of 0.2 M PADS in 1:1 3-picoline/CH₃CN were used as a sulfurization reagent with a 2 minute contact time. A solution of tert-butyl hydroperoxide/acetonitrile/water (10:87:3) was used to oxidize the internucleoside linkages from phosphites to phosphates. The step-wise coupling efficiencies were more than 97%. After completion of the synthesis, the solid support was suspended in aqueous ammonium hydroxide (30 wt. %, 40 mL for 40 μmol synthesis) and heated at 55° C. for 72 hours. The solid support was then filtered and the filtrate was concentrated to dryness. The residue was dissolved in 0.1 M aqueous ammonium acetate and purified by High Performance Liquid Chromatography (HPLC) on a strong anion exchange column (Source Q, Amersham Pharmacia Biotech (Uppsala, Sweden), 2.54×8 cm, 41.2 mL, 30 μm, A=100 mM ammonium acetate, 30% aqueous acetonitrile, B=1.5 M NaBr in A, 0 to 60% B in 40 min, Flow 1.5 mL min⁻¹, λ=260 nm). Modified oligonucleotides were desalted by HPLC on reverse phase column. The modified oligonucleotides were isolated in 10% yield based on the loading of the solid support. The modified oligonucleotides were characterized by ion-pair-HPLC-MS analysis with Agilent 1100 MSD system.

| SEQ ID NO/ ISIS NO | Composition (5' to 3') | Calcd Mass | Found Mass |
|---|---|---|---|
| 06/404973 | P-C$_t$T$_t$TAGCACTGGCC$_t$T$_t$ | 4655.9 | 4655.1 |

All internucleoside linkages are phosphorothioates, P indicates a phosphate group, nucleosides not followed by a subscript are β-D-2'-deoxyribonucleosides and nucleosides followed by a subscript t indicates a tricyclic nucleoside having formula Ia:

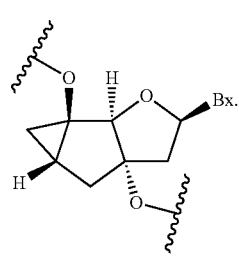

Ia

Example 19

Gapped Oligomeric Compounds Targeted to PTEN

In Vitro Study

In accordance with the present disclosure, oligomeric compounds were synthesized and tested for their ability to reduce PTEN expression over a range of doses. b.END cells were treated with 2-10-2 gapped oligomers having either tricyclic nucleosides (404973) or 2'-O-MOE modified nucleosides (392753) in wings. A 5-10-5 gapped oligomer having 2'-O-MOE modified nucleosides in wings (116847) was also included for comparison. A dose comparison was evaluated with dose concentrations of 0.3125, 0.625, 1.25, 2.5, 5, 10, 20 and 40 nM using methods described herein. Expression levels of PTEN were determined using real-time PCR and normalized to RIBOGREEN™ using methods described herein. The percent inhibition of PTEN mRNA was determined Resulting dose-response curves were used to determine the IC₅₀. Tm's were assessed in 100 mM phosphate buffer, 0.1 mM EDTA, pH 7, at 260 nm using 4 μM modified oligomers and 4 μM complementary RNA. The activities are listed below.

| SEQ ID NO/ ISIS NO | Composition (5' to 3') | $IC_{50}$ | Tm ° C. |
|---|---|---|---|
| 05/116847 | $^{me}C_eT_eG_e{}^{me}C_eT_eAG^{me}C^{me}CT^{me}CTGGAT_eT_eT_eG_eA_e$ | 11.1 | 67.9 |
| 06/392753 | $C_eT_eTAGCACTGGCC_eT_e$ | >40 | 51.3 |
| 06/404973 | $P-C_tT_tTAGCACTGGCC_tT_t$ | 19.4 | 52.7 |

Each internucleoside linking group is a phosphorothioate, nucleosides not followed by a subscript are β-D-2'-deoxyribonucleosides, P indicates a phosphate group, superscript Me indicates that the following C is a 5-methyl C, subscript e indicates that the preceding nucleoside is a 2'-O(CH$_2$)$_2$—O—CH$_3$ (MOE) substituted nucleoside and nucleosides followed by a subscript t are tricyclic nucleosides having formula Ia as illustrated in Example 18.

| | % Inhibition of PTEN mRNA @ Dose (nM) | | | | | | | |
|---|---|---|---|---|---|---|---|---|
| ISIS NO | 0.3125 | 0.625 | 1.25 | 2.5 | 5 | 10 | 20 | 40 |
| 116847 | 2 | 17 | 13 | 35 | 40 | 51 | 55 | 68 |
| 392753 | 4 | 10 | 12 | 12 | 24 | 32 | 23 | 30 |
| 404973 | 0 | 0 | 4 | 16 | 29 | 41 | 51 | 59 |

Example 20

Gapped Oligomeric Compounds Targeted to PTEN

In Vivo Study

In accordance with the present disclosure, oligomeric compounds were synthesized and tested for their ability to reduce PTEN expression in vivo at doses of 20 and 60 mg/kg. Six week old male Balb/c mice (Jackson Laboratory, Bar Harbor, Me.) were administered a single intraperitoneal (i.p) injection at either 20 or 60 mg/kg of a 2-10-2 gapped oligomer having either tricyclic nucleosides (404973), 2'-O-MOE modified nucleosides (392753) or LNA nucleosides (392063) in the wings. A 5-10-5 gapped oligomer having 2'-O-MOE modified nucleosides in wings (116847) was also included for comparison.

Each dose group consisted of four animals. The mice were sacrificed 48 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. Results are listed below as the average % inhibition of mRNA expression for each treatment group, normalized to saline-injected control.

Liver transaminase levels, alanine aminotranferease (ALT) and aspartate aminotransferase (AST), in serum were also measured relative to saline injected mice. The approximate liver transaminase levels are listed below.

| SEQ ID NO/ ISIS NO | Composition (5' to 3') | % UTC @ 20 mg/kg | % UTC @ 60 mg/kg |
|---|---|---|---|
| 05/116847 | $^{me}C_eT_eG_e{}^{me}C_eT_eAG^{me}C^{me}CT^{me}CTGGAT_eT_eT_eG_eA_e$ | 48 | 18 |
| 06/392753 | $C_eT_eTAGCACTGGCC_eT_e$ | 84 | 68 |
| 06/404973 | $P-C_tT_tTAGCACTGGCC_tT_t$ | not tested | 10 |
| 06/392063 | $^{me}C_lT_lTAGCACTGGC^{me}C_lT_l$ | 14 | 8 |

Each internucleoside linking group is a phosphorothioate, nucleosides not followed by a subscript are β-D-2'-deoxyribonucleosides, P indicates a phosphate group, superscript Me indicates that the following C is a 5-methyl C, subscript e indicates that the preceding nucleoside is a 2'-O(CH$_2$)$_2$—O—CH$_3$ (MOE) substituted nucleoside, subscript la indicates that the preceding nucleoside is a bicyclic nucleoside having a 4'-CH$_2$—O-2' bridge (LNA) and nucleosides followed by a subscript t are tricyclic nucleosides having formula I as illustrated in Example 18.

| SEQ ID NO./ ISIS NO. | AST @ 20 mg/kg | AST @ 60 mg/kg | ALT @ 20 mg/kg | ALT @ 60 mg/kg |
|---|---|---|---|---|
| 05/116847 | 116.5 | 77 | 41 | 30 |
| 06/392753 | 64.5 | 77.25 | 25 | 27.5 |
| 06/404973 | not tested | 67.25 | not tested | 26 |
| 06/392063 | 55.75 | 598.25 | 27.75 | 488.5 |

Transaminase levels for mice treated with the modified oliomeric compounds were not indicative of hepatotoxicity.

The effects on liver, spleen and kidney weights were also determined and have are listed below.

| SEQ ID NO./ ISIS NO. | Liver wt. @ 20 mg/kg | Liver wt. @ 60 mg/kg | Kidney wt. @ 32 mg/kg | Kidney wt. @ 100 mg/kg |
|---|---|---|---|---|
| Saline | 1.00 | 1.00 | 1.00 | |
| 05/116847 | 1.15 | 1.10 | 1.02 | 1.01 |
| 06/392753 | 1.04 | 1.29 | 1.02 | 1.00 |
| 06/404973 | not tested | 1.10 | not tested | 0.98 |
| 06/392063 | 1.22 | 1.25 | 1.02 | 1.02 |

| SEQ ID NO./ ISIS NO. | Spleen wt. @ 20 mg/kg | Spleen wt. @ 60 mg/kg | Body wt. @ 32 mg/kg | Body wt. @ 100 mg/kg |
|---|---|---|---|---|
| Saline | 1.00 | 1.00 | 1.00 | |
| 05/116847 | 0.99 | 0.99 | 1.06 | 1.06 |
| 06/392753 | 1.02 | 1.11 | 1.05 | 1.05 |
| 06/404973 | not tested | 0.99 | not tested | 1.06 |
| 06/392063 | 0.99 | 1.12 | 1.05 | 0.99. |

Example 21

Gapped Oligomeric Compounds Targeted to PTEN

In Vivo Study

Six week old Balb/c mice (Jackson Laboratory, Bar Harbor, Me.) were injected twice per week for three weeks with the gapped oligomeric compounds shown below. The oligomeric compounds were targeted to PTEN at doses of 0.47, 1.5, 4.7 or 15 mg/kg. The mice were sacrificed 48 hours following last administration. Liver tissues were homogenized and mRNA levels were quantitated using real-time PCR as described herein. Plasma chemistry analysis was completed.

| SEQ ID NO./ ISIS NO. | Composition (5' to 3') | $ED_{50}$ |
|---|---|---|
| 06/404973 | P-$C_fT_f$TAGCACTGGCC$_fT_f$ | 9.0 |
| 06/392063 | $^{me}C_fT_f$TAGCACTGGC$^{me}C_fT_f$ | 3.4 |
| 05/116847 | $^{me}C_eT_eG_e{}^{me}C_eT_eAG^{me}C^{me}CT$ $^{me}CTGGAT_eT_eT_eG_eA_e$ | 9.5* |

*This data is from a previous study wherein the ALTs and ASTs were normal with the highest dosing at 3.2 µmol/kg.

Each internucleoside linking group is a phosphorothioate, nucleosides not followed by a subscript are β-D-2'-deoxyribonucleosides, P indicates a phosphate group, superscript Me indicates that the following C is a 5-methyl C, nucleosides followed by a subscript e indicates that the preceding nucleoside is a 2'-O(CH$_2$)$_2$—O—CH$_3$ (MOE) substituted nucleoside and nucleosides followed by a subscript t are tricyclic nucleosides having formula Ia as illustrated in Example 18

| SEQ ID NO./ ISIS NO. | AST @ 0.47 mg/kg | AST @ 1.5 mg/kg | ALT @ 4.7 mg/kg | ALT @ 15 mg/kg |
|---|---|---|---|---|
| 06/404973 | 20 | 18 | 18 | 16 |
| 06/392063 | 19.5 | 30 | 18 | 168. |

All publications, patents, and patent applications referenced in the present disclosure are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An oligomeric compound comprising at least one tricyclic nucleoside having formula II:

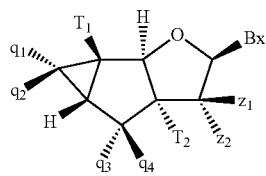

II wherein independently for each of said tricyclic nucleosides having formula II:
Bx is a heterocyclic base moiety;
one of $T_1$ and $T_2$ is an internucleoside linking group attaching said tricyclic nucleoside of formula II to said oligomeric compound and the other of $T_1$ and $T_2$ is hydroxyl, a protected hydroxyl, a 5' or 3'-terminal group selected from one or more conjugate groups, capping groups and phosphate moieties or an internucleoside linking group attaching said tricyclic nucleoside of formula II to said oligomeric compound;
$q_1$, $q_2$, $q_3$ and $q_4$ are each H;
$z_1$ is H and $z_2$ is F; and wherein said oligomeric compound comprises from about 8 to about 40 linked monomeric subunits and is complementary to at least a portion of a target RNA.

2. The oligomeric compound of claim 1 wherein each Bx is, independently, uracil, thymine, cytosine, 5-methylcytosine, adenine or guanine.

3. The oligomeric compound of claim 1 wherein said oligomeric compound further comprises said 5' or 3'-terminal group.

4. The oligomeric compound of claim 1 wherein each monomeric subunit is, independently, a β-D-2'-deoxyribonucleoside or a tricyclic nucleoside having formula II.

5. The oligomeric compound of claim 1 wherein each linked monomeric subunit that is not a β-D-2'-deoxyribonucleoside or a tricyclic nucleoside having formula II is a modified nucleoside independently selected from a bicyclic modified nucleoside, a 2'-modified nucleoside, a 4'-thio modified nucleoside or a 4'-thio-2'modified nucleoside.

6. The oligomeric compound of claim 1 wherein said oligomeric compound comprises a motif selected from a gapped motif, a hemimer motif, a blockmer motif, a fully modified motif, a positionally modified motif and an alternating motif.

7. The oligomeric compound of claim 1 wherein said oligomeric compound comprises a gapped oligomeric compound comprising two external regions separated by an internal region wherein each external region independently comprises from 1 to 5 contiguous tricyclic nucleosides of formula II and the internal region comprises from 6 to about 23 contiguous monomeric subunits independently selected β-D-ribonucleosides and β-D-2'-deoxyribonucleosides.

8. The oligomeric compound of claim 7 wherein essentially each monomeric subunit in the internal region is a β-D-2'-deoxyribonucleoside.

9. The oligomeric compound of claim 7 wherein the internal region comprises from about 8 to about 12 β-D-2'-deoxyribonucleosides.

10. The oligomeric compound of claim 9 wherein each external region comprises from 1 to 3 tricyclic nucleosides of formula II.

11. The oligomeric compound of claim 10 wherein the internal region comprises 10 β-D-2'-deoxyribonucleosides.

12. The oligomeric compound of claim 1 wherein said oligomeric compound comprises a 5'-terminal tricyclic nucleoside of formula II wherein $T_1$ is a 5'-phosphate moiety.

13. The oligomeric compound of claim 1 wherein each internucleoside linking group is, independently, a phosphodiester or a phosphorothioate.

14. The oligomeric compound of claim 1 comprising from 10 to about 16 linked monomeric subunits.

15. The oligomeric compound of claim 1 comprising from 18 to about 21 linked monomeric subunits.

16. A tricyclic nucleoside having formula III:

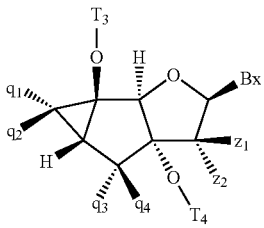

wherein:
Bx is a heterocyclic base moiety;
one of $T_3$ and $T_4$ is H or a hydroxyl protecting group and the other of $T_3$ and $T_4$ is H, a hydroxyl protecting group or a reactive phosphorus group;
$q_1$, $q_2$, $q_3$ and $q_4$ are each H; and
$z_1$ is H and $z_2$ is F.

17. The tricyclic nucleoside of claim 16 wherein Bx is uracil, thymine, cytosine, 5-methylcytosine, adenine or guanine.

18. The tricyclic nucleoside of claim 16 wherein $T_3$ is 4,4'-dimethoxytrityl and $T_4$ is diisopropylcyanoethoxy phosphoramidite.

* * * * *

SEQUENCE LISTING

```
<160> NUMBER OF SEQ ID NOS: 6

<210> SEQ ID NO 1
<211> LENGTH: 3160
<212> TYPE: DNA
<213> ORGANISM: Homo sapiens

<400> SEQUENCE: 1
cctcccctcg cccggcgcgg tcccgtccgc ctctcgctcg cctcccgcct cccctcggtc    60
ttccgaggcg cccgggctcc cggcgcggcg gcggaggggg cgggcaggcc ggcgggcggt   120
gatgtggcag gactctttat gcgctgcggc aggatacgcg ctcggcgctg ggacgcgact   180
gcgctcagtt ctctcctctc ggaagctgca gccatgatgg aagtttgaga gttgagccgc   240
tgtgaggcga ggccgggctc aggcgaggga gatgagagac ggcggcggcc gcggcccgga   300
gcccctctca gcgcctgtga gcagccgcgg gggcagcgcc ctcggggagc cggccggcct   360
gcggcggcgg cagcggcggc gtttctcgcc tcctcttcgt cttttctaac cgtgcagcct   420
cttcctcggc ttctcctgaa agggaaggtg gaagccgtgg gctcgggcgg gagccggctg   480
aggcgcggcg gcggcggcgg cggcacctcc cgctcctgga gcgggggggga gaagcggcgg   540 cggcggcggc cgcggcggct gcagctccag ggaggggggtc tgagtcgcct gtcaccattt   600
ccagggctgg gaacgccgga gagttggtct ctcccttct actgcctcca acacggcggc   660 ggcggcggc gcacatccag ggacccgggc cggttttaaa cctcccgtcc gccgccgccg   720 cacccccgt ggcccgggct ccggaggccg ccggcggagg cagccgttcg gaggattatt   780
cgtcttctcc ccattccgct gccgccgctg ccaggcctct ggctgctgag gagaagcagg   840
cccagtcgct gcaaccatcc agcagccgcc gcagcagcca ttacccggct gcggtccaga   900
gccaagcggc ggcagagcga ggggcatcag ctaccgccaa gtccagagcc atttccatcc   960
tgcagaagaa gccccgccac cagcagcttc tgccatctct ctcctccttt ttcttcagcc  1020
acaggctccc agacatgaca gccatcatca aagagatcgt tagcagaaac aaaaggagat  1080
atcaagagga tggattcgac ttagacttga cctatattta tccaaacatt attgctatgg  1140
gatttcctgc agaaagactt gaaggcgtat acaggaacaa tattgatgat gtagtaaggt  1200
ttttggattc aaagcataaa aaccattaca agatatacaa tctttgtgct gaaagacatt  1260
```

```
atgacaccgc caaatttaat tgcagagttg cacaatatcc ttttgaagac cataacccac   1320
cacagctaga acttatcaaa cccttttgtg aagatcttga ccaatggcta agtgaagatg   1380
acaatcatgt tgcagcaatt cactgtaaag ctggaaaggg acgaactggt gtaatgatat   1440
gtgcatattt attacatcgg ggcaaatttt taaaggcaca agaggcccta gatttctatg   1500
gggaagtaag gaccagagac aaaaagggag taactattcc cagtcagagg cgctatgtgt   1560
attattatag ctacctgtta aagaatcatc tggattatag accagtggca ctgttgtttc   1620
acaagatgat gtttgaaact attccaatgt tcagtggcgg aacttgcaat cctcagtttg   1680
tggtctgcca gctaaaggtg aagatatatt cctccaattc aggacccaca cgacgggaag   1740
acaagttcat gtactttgag ttccctcagc cgttacctgt gtgtggtgat atcaaagtag   1800
agttcttcca caaacagaac aagatgctaa aaaaggacaa aatgtttcac ttttgggtaa   1860
atacattctt cataccagga ccagaggaaa cctcagaaaa agtagaaaat ggaagtctat   1920
gtgatcaaga aatcgatagc atttgcagta tagagcgtgc agataatgac aaggaatatc   1980
tagtacttac tttaacaaaa aatgatcttg acaaagcaaa taaagacaaa gccaaccgat   2040
acttttctcc aaattttaag gtgaagctgt acttcacaaa aacagtagag gagccgtcaa   2100
atccagaggc tagcagttca acttctgtaa caccagatgt tagtgacaat gaacctgatc   2160
attatagata ttctgacacc actgactctg atccagagaa tgaaccttt gatgaagatc   2220 agcatacaca aattacaaaa gtctgaattt tttttttatca agagggataa acaccatga   2280 aaataaactt gaataaactg aaaatggacc tttttttttt taatggcaat aggacattgt   2340
gtcagattac cagttatagg aacaattctc ttttcctgac caatcttgtt ttaccctata   2400
catccacagg gttttgacac ttgttgtcca gttgaaaaaa ggttgtgtag ctgtgtcatg   2460
tatatacctt tttgtgtcaa aaggacattt aaaattcaat taggattaat aaagatggca   2520
ctttcccgtt ttattccagt tttataaaaa gtggagacag actgatgtgt atacgtagga   2580 atttttcct tttgtgttct gtcaccaact gaagtggcta aagagctttg tgatatactg   2640
gttcacatcc tacccctttg cacttgtggc aacagataag tttgcagttg gctaagagag   2700
gtttccgaaa ggttttgcta ccattctaat gcatgtattc gggttagggc aatggagggg   2760
aatgctcaga aaggaaataa ttttatgctg gactctggac catataccat ctccagctat   2820
ttacacacac ctttctttag catgctacag ttattaatct ggacattcga ggaattggcc   2880
gctgtcactg cttgttgttt gcgcattttt ttttaaagca tattggtgct agaaaaggca   2940
gctaaaggaa gtgaatctgt attggggtac aggaatgaac cttctgcaac atcttaagat   3000
ccacaaatga agggatataa aaataatgtc ataggtaaga aacacagcaa caatgactta   3060
accatataaa tgtggaggct atcaacaaag aatgggcttg aaacattata aaaattgaca   3120
atgatttatt aaatatgttt tctcaattgt aaaaaaaaaa                        3160
```

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                        26

<210> SEQ ID NO 3

```
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                         25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                    30

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ctgctagcct ctggatttga                                               20

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 6
cttagcactg gcct                                                     14
```